US009258995B2

(12) United States Patent
MacMillan-Crow

(10) Patent No.: US 9,258,995 B2
(45) Date of Patent: Feb. 16, 2016

(54) ORGAN COLD STORAGE COMPOSITION AND METHODS OF USE

(75) Inventor: Lee Ann MacMillan-Crow, Little Rock, AR (US)

(73) Assignee: BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 13/476,586

(22) Filed: May 21, 2012

(65) Prior Publication Data

US 2012/0244518 A1 Sep. 27, 2012

Related U.S. Application Data

(63) Continuation-in-part of application No. PCT/US2010/057246, filed on Nov. 18, 2010.

(60) Provisional application No. 61/262,971, filed on Nov. 20, 2009.

(51) Int. Cl.
*A01N 1/02* (2006.01)

(52) U.S. Cl.
CPC .................................. *A01N 1/0226* (2013.01)

(58) Field of Classification Search
None
See application file for complete search history.

(56) References Cited

U.S. PATENT DOCUMENTS

| | | | |
|---|---|---|---|
| 6,054,261 A | 4/2000 | Masterson | |
| 6,468,789 B1 * | 10/2002 | Baysal et al. | 435/320.1 |
| 6,569,683 B1 * | 5/2003 | Ochi et al. | 436/63 |
| 2004/0132111 A1 * | 7/2004 | Banan et al. | 435/7.2 |
| 2005/0136391 A1 | 6/2005 | Steinhardt | |
| 2005/0164156 A1 * | 7/2005 | Masaki et al. | 435/1.1 |
| 2006/0166182 A1 | 7/2006 | Weinberg | |
| 2007/0148628 A1 | 6/2007 | Young | |
| 2008/0275005 A1 | 11/2008 | Murphy | |
| 2008/0289053 A1 * | 11/2008 | Wallace et al. | 800/3 |

FOREIGN PATENT DOCUMENTS

| | | |
|---|---|---|
| WO | WO 02/30452 | 4/2002 |
| WO | WO 2008/106724 | 9/2008 |
| WO | 2011063130 | 5/2011 |
| WO | 2011108946 | 9/2011 |

OTHER PUBLICATIONS

Lowes et al, The mitochondria-targeted antioxidant MitoQ protects against organ damage in a lipopolysaccharide-peptidoglycan model of sepsis, 2008, Free Radical Biology & Medicine 45:1559-1565.*
Ligeret et al, Antioxidant and mitochondrial protective effects of silibinin in cold preservation—warm reperfusion liver injury, 2008, Journal of Ethnopharmacology 115: 507-514.*
Tauskela, MitoQ—a mitochondria-targeted antioxidant, 2007, Investigational Drugs Journal 10(6):399-412.*
Szeto, Mitochondria-Targeted Cytoprotective Peptides for Ischemia—Reperfusion Injury, 2008, Antioxidants & Redox Signaling, 10(3) : 601-619.*
Murphy et al, Targeting Antioxidants to Mitochondria by Conjugation to Lipophilic Cations, Annu. Rev. Pharmacol. Toxicol. 2007. 47:629-56.*
Murphy, Targeting antioxidants to mitochondria by conjugation to lipophilic cations, Annu Rev Pharmacol Toxicol, 2007, 47:629-56.
Szeto, Mitochondria-targeted peptide antioxidants: novel neuroprotective agents, The AAPS Journal, 2006, 8(3) Article 62.
International Search Report and Written Opinion from related international application No. PCT/US2010/057246 dated Jan. 26, 2011, 7 pages.
Thorniley, Non-invasive measurement of respiratory chain dysfunction following hypothermic renal storage and transplatation, Kidney International, 1994 vol. 45, pp. 1489-1496.
Perico, Tackling the Shortage of Donor Kidneys: How to Use the Best that We Have, Am J Nephrol, 2003, vol. 23, pp. 245-259.
Sammut, et al., "Impairment of Hepatic Mitochondrial Respiratory Function Following Storage and Orthotopic Transplantation of Rat Livers," Cryobiology, 1998, pp. 49-60, Article CY972063, vol. 36.
Schimke, et al., "Oxidative Stress in the Human Heart Is Associated With Changes in the Antioxidative Defense as Shown After Heart Transplantation," Molecular and Cellular Biochemistry, 2000, pp. 89-96, vol. 204.
Saba, et al., "Cold Preservation Mediated Renal Injury: Involvement of Mitochondrial Oxidative Stress," Renal Failure, 2008, pp. 125-133, vol. 30.
New Zealand Intellectual Property Office, First Examination Report, NZ Publication No. 599592, dated Feb. 15, 2013, 2 pages.
New Zealand Intellectual Property Office, Second Examination Report, NZ Publication No. 599592, dated Aug. 7, 2013, 2 pages.
European Patent Office, European Search Report, European Patent Application No. 10 832 186.0, dated Jan. 31, 2014, 10 pages.
Belzer, Principles of Solid-Organ Preservation by Cold Storage, Transplantation, Apr. 1988, pp. 673-676, vol. 45, No. 4.
Guibert, Organ Preservation: Current Concepts and New Strategies for the Next Decade, Transfusion Medicine and Hemotherapy, Mar. 21, 2011, pp. 125-142, vol. 28.
Martin, Primary Cause of Unsuccessful Liver and Heart Preservation: Cold Sensitivity of the ATPase System, Ann. Surg., Jan. 1972, pp. 111-117, vol. 175, No. 1.
Rauen, New Insights into the Cellular and Molecular Mechanisms of Cold Storage Injury, Journal of Investigative Medicine, Jul. 2004, pp. 299-309, vol. 52, No. 5.
Office Action dated Sep. 29, 2014 from related EP Application No. 10 832 186.0, 8 pages.

* cited by examiner

*Primary Examiner* — Sharmila G. Landau
*Assistant Examiner* — Stephanie McNeil
(74) *Attorney, Agent, or Firm* — Polsinelli PC

(57) ABSTRACT

The present invention provides compositions and methods for decreasing oxidative damage to an organ during cold storage.

**17 Claims, 33 Drawing Sheets
(19 of 33 Drawing Sheet(s) Filed in Color)**

ORGAN COLD STORAGE COMPOSITION AND METHODS OF USE

FIELD OF THE INVENTION

The present invention provides compositions and methods for decreasing oxidative damage to an organ.

BACKGROUND OF THE INVENTION

Increased oxidant production contributes to organ damage prior to and following organ transplantation. Most organ transplants are performed using deceased donor organs that undergo an extensive period of cold preservation/ischemia (while a suitable transplant recipient is found) as well as a period of warm ischemia during the surgical procedure. Damage to the organ during this time frame limits the number of organs available for transplant and can inhibit the function of a transplanted organ. Consequently, there is a need in the art for compositions and methods for decreasing the oxidative damage to an organ during cold storage. This could lead to increased numbers of organs available for transplant (reduce the number of discarded organs) and better performance of transplanted organs.

SUMMARY OF THE INVENTION

One aspect of the present invention encompasses a method of reducing oxidative damage to an organ during cold storage. The method comprises contacting the organ with a composition comprising a mitochondrial specific antioxidant and an organ preservation solution.

Another aspect of the present invention encompasses a method of reducing oxidative damage to a kidney during cold storage. The method comprises contacting the kidney with a composition comprising a mitochondrial specific antioxidant and an organ preservation solution.

Still another aspect of the present invention encompasses a composition. The composition comprises a mitochondrial specific antioxidant and an organ preservation solution.

Other aspects and iterations of the invention are described more thoroughly below.

REFERENCE TO COLOR FIGURES

The application file contains at least one photograph executed in color. Copies of this patent application publication with color photographs will be provided by the Office upon request and payment of the necessary fee.

DETAILED DESCRIPTION OF THE INVENTION

Figure 1:
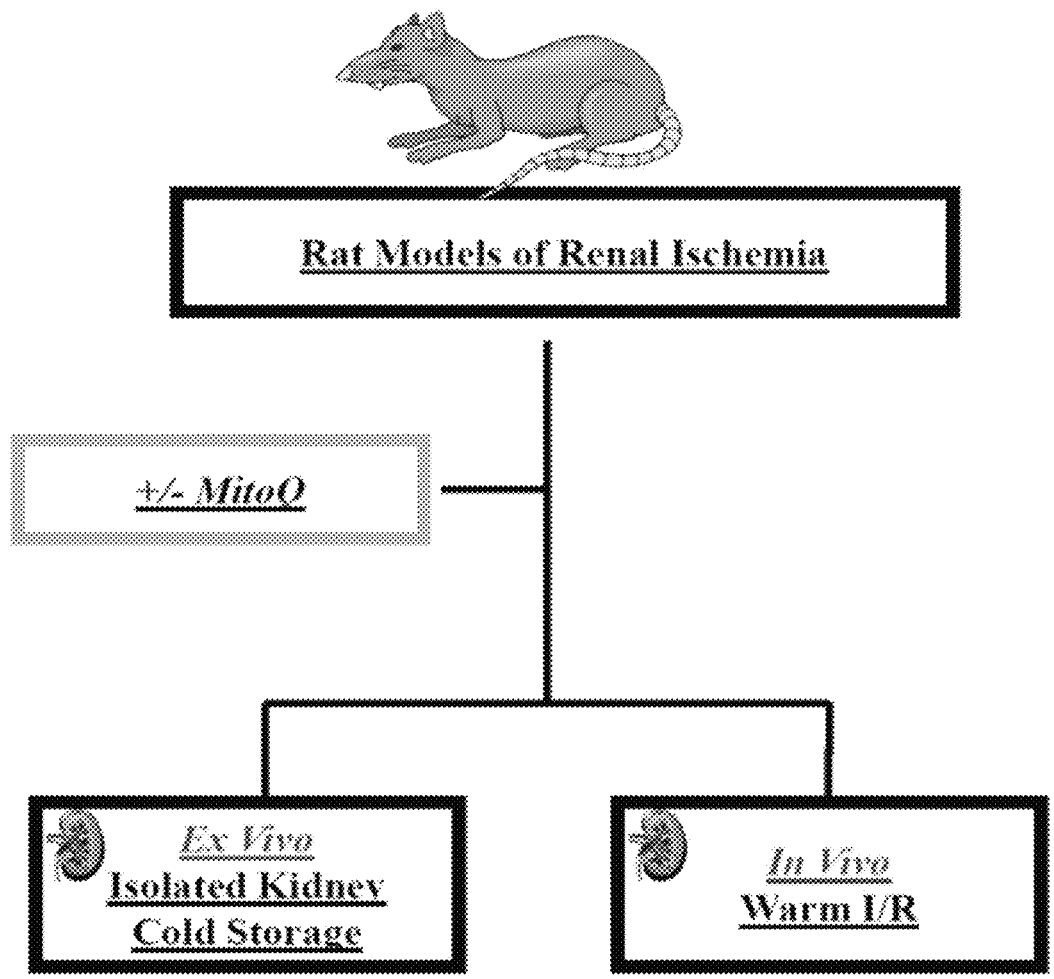
FIG. 1 depicts a schematic showing an experimental design to evaluate the use of MitoQ in organ preservation.
Figure 2:
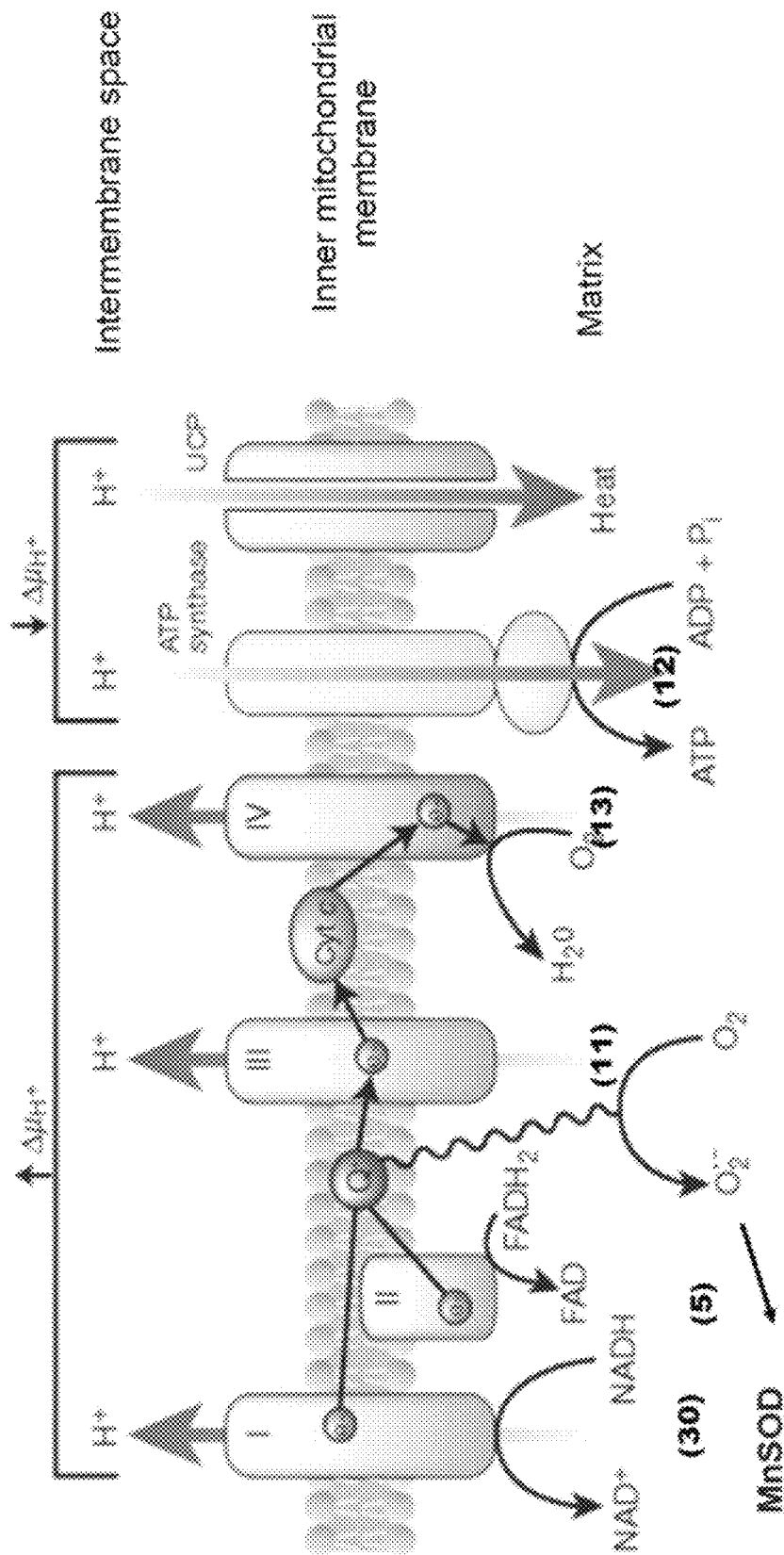
FIG. 2 depicts a schematic of mitochondrial electron transport complexes.

The present invention provides a composition for the cold storage of an organ. The composition comprises a mitochondrial specific antioxidant. The invention also encompasses methods of using the composition, including a method of decreasing oxidative damage to an organ or tissue.

I. Composition

One aspect of the present invention encompasses a composition for decreasing the oxidative damage of an organ or tissue during cold storage. Generally speaking, the composition comprises a mitochondrial specific antioxidant. Stated another way, the composition comprises an antioxidant that is targeted to mitochondria. In one embodiment, the mitochondrial specific antioxidant is MitoQ. The term "MitoQ" refers to the ubiquinone antioxidant moiety of coenzyme Q10 covalently attached to a lipophillic triphenylphosphonium cation. The structure of MitoQ is shown in Formula I below:

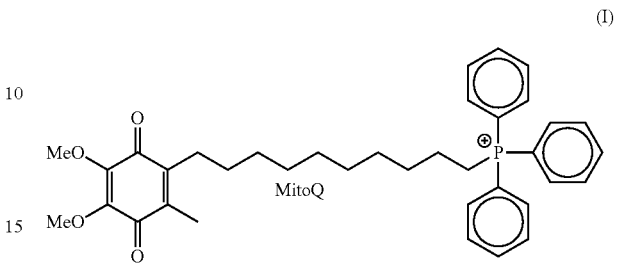

(I)

Other mitochondria specific antioxidants are known in the art. See for instance, Murphy M P and Smith R A (2007) 47:629-56 and Szeto (2006) 8(3):E521, hereby incorporated by reference in their entirety.

In addition to a mitochondrial specific antioxidant, a composition of the invention may also comprise one or more than one organ preservation solution. As used herein, an "organ preservation solution" refers to a solution known in the art for organ or tissue perfusion, preservation or reperfusion. Such solutions may include but are not limited to Celsior solution, Krebs-Henseleit solution, normal saline solution, University of Wisconsin solution, St. Thomas II solution, Collins solution, Stanford solution, or combinations thereof. The compositions may also contain one or more than one agent known in the art for protecting tissue from damage during transplantation or from acute ischemia due to injury or surgery. Such agents may include but are not limited to protein kinase C inhibitors, bupivacaine, levo-bupivacaine, etidocaine, ropivacaine, or tetracaine, such as described in detail in U.S. Pat. App. Pub. Nos. 20070148628 and 20060166182, each of which is hereby incorporated by reference in its entirety.

The amount of mitochondrial specific antioxidant in a composition of the invention can and will vary depending, in part, upon the preservation solution used and the organ being preserved. One of skill in the art can perform routine optimization testing to determine the optimum amount for a specific application. In one embodiment where the mitochondrial specific antioxidant is MitoQ, the amount may generally be between about 10 μM and about 200 μM. For instance, the amount of MitoQ may be about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 μM.

II. Methods

Another aspect of the invention encompasses a method for decreasing oxidative damage to an organ. Generally speaking, the method comprises contacting the organ with a composition comprising a mitochondrial specific antioxidant.

Suitable compositions of the invention are described in section I above. As used herein, "decreased oxidative damage" or "reduced oxidative damage" may be measured in comparison to an organ treated under similar conditions, but that is not exposed to a composition comprising a mitochondrial specific antioxidant. For instance, the control organ may be treated under similar conditions, but the organ is exposed to a composition comprising decyltriphenylphosphonium bromide (decylTPP) which has a similar chemical structure to MitoQ but without the antioxidant ubiquinol moiety.

In an exemplary embodiment, the invention encompasses a method for decreasing oxidative damage to an organ during cold storage. Such a method comprises contacting the organ subjected to cold storage with a composition comprising a mitochondrial specific antioxidant. Such methods may increase the number of organs available for transplant by decreasing the number of organs lost to oxidative damage. Such methods may also improve the post-transplant performance of an organ by decreasing the oxidative damage to the organ. In each of the above embodiments, the mitochondrial specific antioxidant may be MitoQ.

In some embodiments, the invention encompasses a method for increasing MnSOD activity in an organ during cold storage. The method comprises contacting the organ with a composition of the invention comprising a mitochondrial specific antioxidant, wherein MnSOD activity is increased in the organ compared to an organ in cold storage that has not been contacted with a composition of the invention. In one variation of the above embodiment, the organ is a kidney. Methods of measuring MnSOD activity are known in the art. In each of the above embodiments, the mitochondrial specific antioxidant may be MitoQ.

In other embodiments, the invention encompasses a method for inhibiting formation of nitrotyrosine in an organ during cold storage. The method comprises contacting the organ with a composition of the invention comprising a mitochondrial specific antioxidant, wherein formation of nitrotyrosine adduct is inhibited in the organ compared to an organ in cold storage that has not been contacted with a composition of the invention. In one variation of the above embodiment, the organ is a kidney. Methods of measuring formation of nitrotyrosine adduct are known in the art. In each of the above embodiments, the mitochondrial specific antioxidant may be MitoQ.

In certain embodiments, the invention encompasses a method for preventing inactivation of mitochondrial complex I activity, complex II activity, complex III activity, complex IV activity, or a combination thereof, in an organ during cold storage. The method comprises contacting the organ with a composition of the invention comprising a mitochondrial specific antioxidant, where contacting the organ with the composition comprising a mitochondrial specific antioxidant activity prevents inactivation of activity of mitochondrial complex I, complex II, complex III, complex IV, or a combination thereof is increased in the organ compared to an organ in cold storage that has not been contacted with a composition of the invention. In one embodiment, contacting the organ with a composition of the invention comprising a mitochondrial specific antioxidant activity prevents inactivation of activity of mitochondrial complex I. In another embodiment, contacting the organ with a composition of the invention comprising a mitochondrial specific antioxidant activity prevents inactivation of activity of mitochondrial complex II. In yet another embodiment, contacting the organ with a composition of the invention comprising a mitochondrial specific antioxidant activity prevents inactivation of activity of mitochondrial complex III. In another embodiment, contacting the organ with a composition of the invention comprising a mitochondrial specific antioxidant activity prevents inactivation of activity of mitochondrial complex IV. In a preferred embodiment, contacting the organ with a composition of the invention comprising a mitochondrial specific antioxidant activity prevents inactivation of activity of mitochondrial complex I and mitochondrial complex II. In another preferred embodiment, contacting the organ with a composition of the invention comprising a mitochondrial specific antioxidant activity prevents inactivation of activity of mitochondrial complex II and mitochondrial complex III. In one variation of the above embodiments, the organ is a kidney. Methods of measuring mitochondrial complex I activity, complex II activity, complex III activity, or complex IV activity are known in the art. In each of the above embodiments, the mitochondrial specific antioxidant may be MitoQ.

In one embodiment, the invention encompasses a method for reducing renal damage during cold organ storage. The method comprises contacting a kidney with a composition of the invention comprising a mitochondrial specific antioxidant. In one variation, the mitochondrial specific antioxidant may be MitoQ. Methods of measuring renal damage are known in the art. For instance, the damage may be measured by determining histopathological changes in the kidney. Non-limiting examples of histopathological changes that may occur during cold storage may include tubular damage such as dilation, brush border loss and cellular debris/cast formation. Alternatively, renal damage may be measured by MnSOD activity, by measuring creatinine clearance, by measuring nitrotyrosine adduct formation, by measuring superoxide generation, or by measuring cell death. In some embodiments, renal damage may be measured by MnSOD activity. In other embodiments, renal damage may be measured by measuring creatinine clearance. In still other embodiments, renal damage may be measured by measuring nitrotyrosine adduct formation. In other embodiments, renal damage may be measured by measuring superoxide generation in the mitochondria. Methods of measuring superoxide generation in the mitochondria are known in the art and may include the use of dyes capable of measuring superoxide in the mitochondria, such as MitoSOX Red. In still other embodiments, renal damage may be measured by measuring nitrotyrosine adduct formation. In yet other embodiments, renal damage may be measured by measuring cell death. For instance, cell death may be measured by TUNEL staining.

In another embodiment, the invention encompasses a method for reducing mitochondrial oxidant production in an organ during cold storage, the method comprising contacting the organ with a composition of the invention comprising a mitochondrial specific antioxidant. In one variation, the mitochondrial specific antioxidant may be MitoQ.

In yet another embodiment, the invention encompasses a method for improving the post-transplant performance of an organ by decreasing oxidative damage to the organ. The method comprises contacting the organ with a composition of the invention comprising a mitochondrial specific antioxidant. In each of the above embodiments, the mitochondrial specific antioxidant may be MitoQ.

A method of the invention may be used to decrease oxidative damage to any tissue or organ subjected to cold storage. Non-limiting examples of such organs may include the heart, kidney, liver, lung, pancreas, intestine, and skin (including face). Non-limiting examples of such tissues may include bone, bone marrow, tendon, cornea, heart valve, or blood vessel. Other examples may include limbs, such as an arm, leg, hand, or foot. Suitable organs may be derived from any eukaryotic organism whose organs are vulnerable to oxidative damage during cold organ storage. Non-limiting examples may include a rodent, a human, a livestock animal, a companion animal, a laboratory animal, or a zoological animal. In one embodiment, suitable organs may be derived from a rodent, e.g. a mouse, a rat, a guinea pig, etc. In another embodiment, suitable organs may be derived from a livestock animal. Non-limiting examples of suitable livestock animals may include pigs, cows, horses, goats, sheep, llamas and alpacas. In yet another embodiment, suitable organs may be derived from a companion animal. Non-limiting examples of companion animals may include pets such as dogs, cats, rabbits, and birds. In another embodiment, suitable organs may be derived from a zoological animal. As used herein, a "zoological animal" refers to an animal that may be found in a zoo. Such animals may include non-human primates, large cats, wolves, and bears.

An organ or tissue may be contacted with a composition comprising a mitochondrial specific antioxidant before removal from a donor, during removal, during cold storage, during warming, during grafting to the recipient, or any combination thereof.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various iterations of the invention.

Example 1

MitoQ Protection Against Renal Damage During Cold Storage

Despite the fact that cold preservation elicits significant kidney injury, cold preservation is essential for successful transplants today because it permits optimal patient selection and transport of kidneys derived from deceased donors. Cold preservation impacts both the quality of transplanted organs and the number of organs available for transplant. Therefore, therapeutic interventions that target the mechanisms by which kidneys are damaged by cold preservation could have a significant impact on the quality and availability of kidneys for transplant.

In these studies the mitochondrial targeted antioxidant mitoquinone (MitoQ) was utilized to study the contribution of mitochondrial superoxide to renal damage during ischemia. MitoQ comprises the ubiquinone antioxidant moiety of coenzyme Q10 covalently attached to a lipophilic triphenylphosphonium cation, which directs the compound to the mitochondria.

Figure 3A:
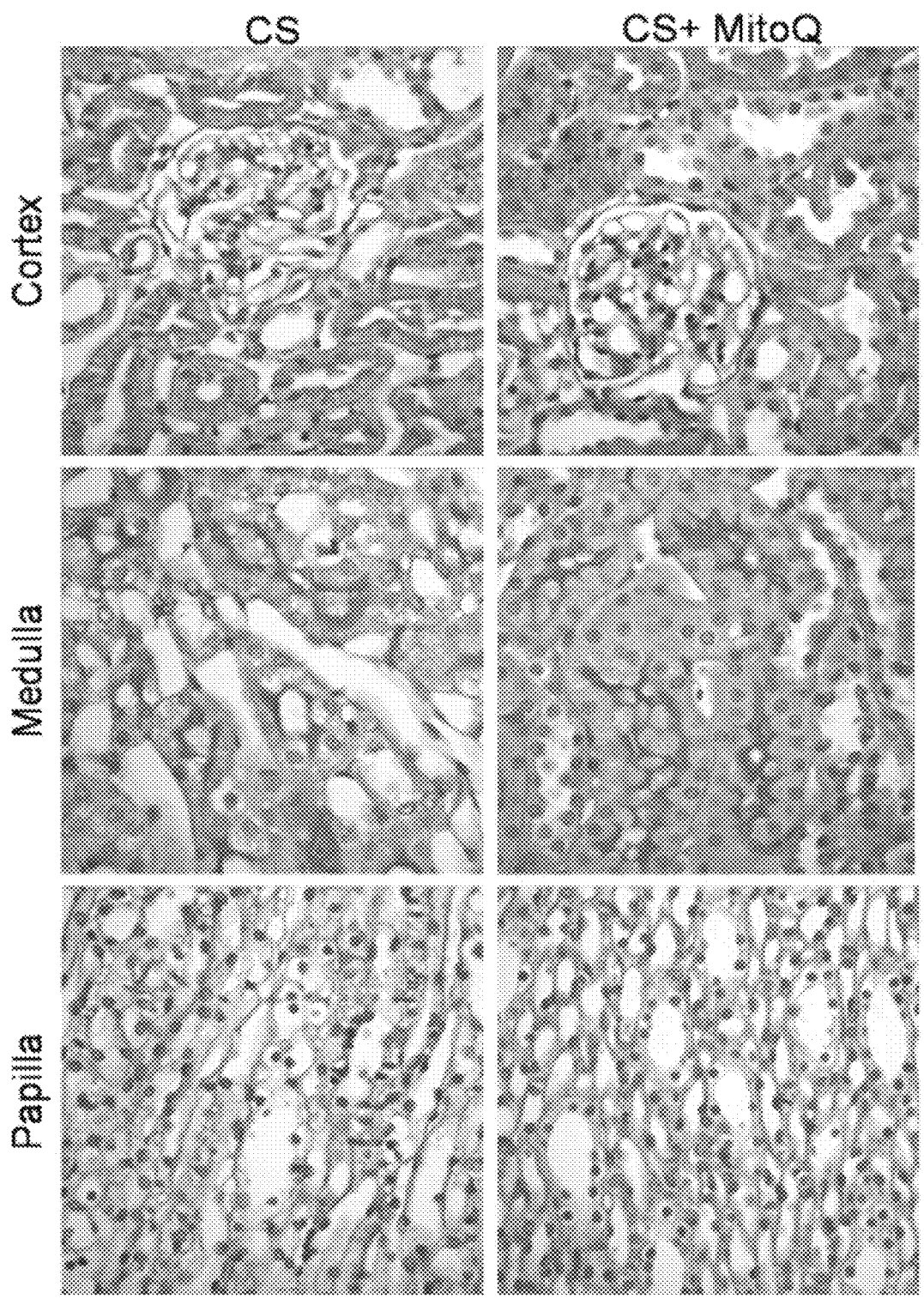
FIG. 3 depicts photomicrographs of rat renal sections placed in cold storage (CS; 4 hr UW; 4° C.) without or with MitoQ (100 μM). Experiments were repeated 3 times with similar results. (A) Periodic acid-Schiff (PAS); (B) Nitrotyrosine staining; (C) TUNEL staining.
Figure 3B:
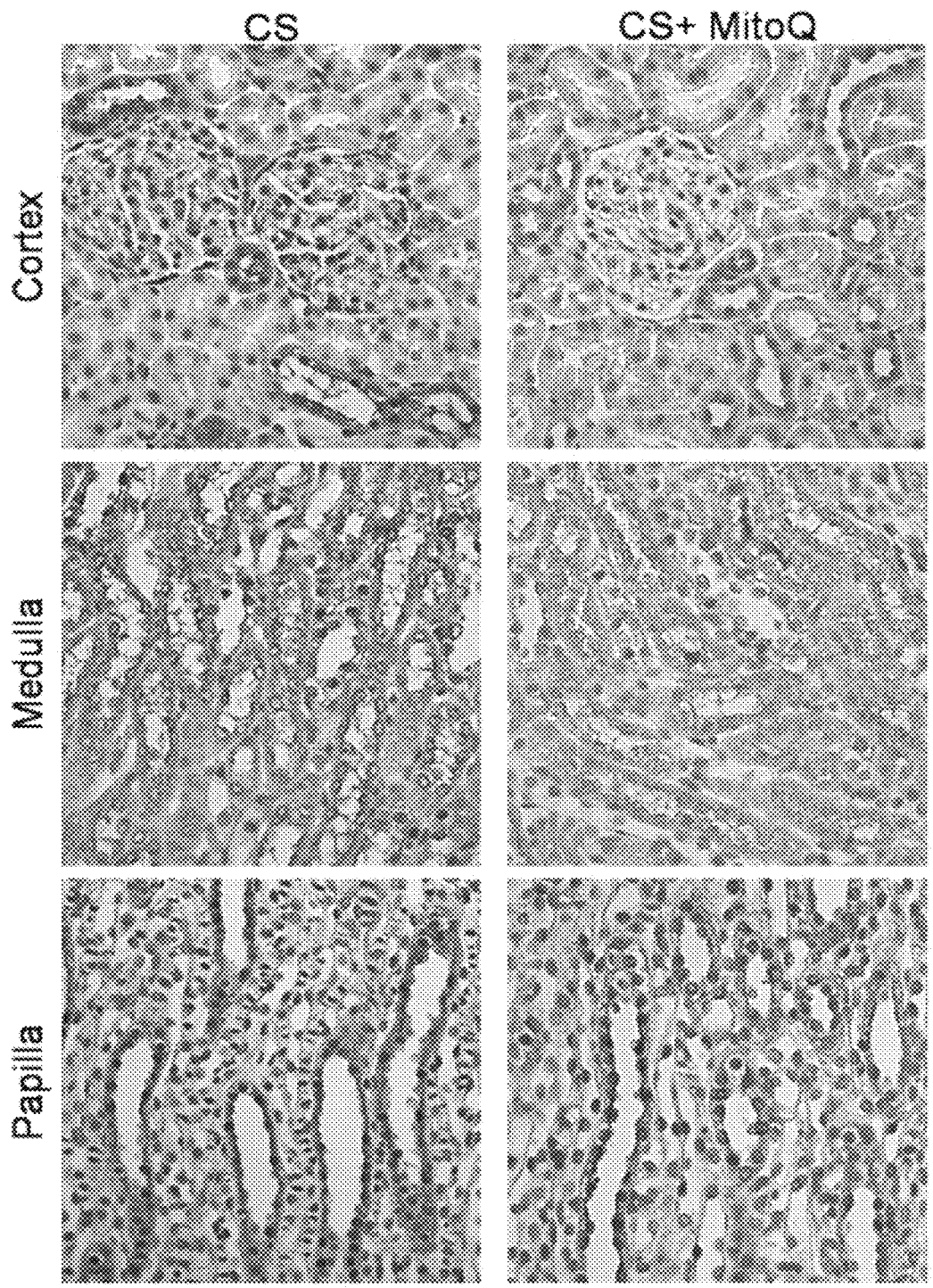
Figure 3C:
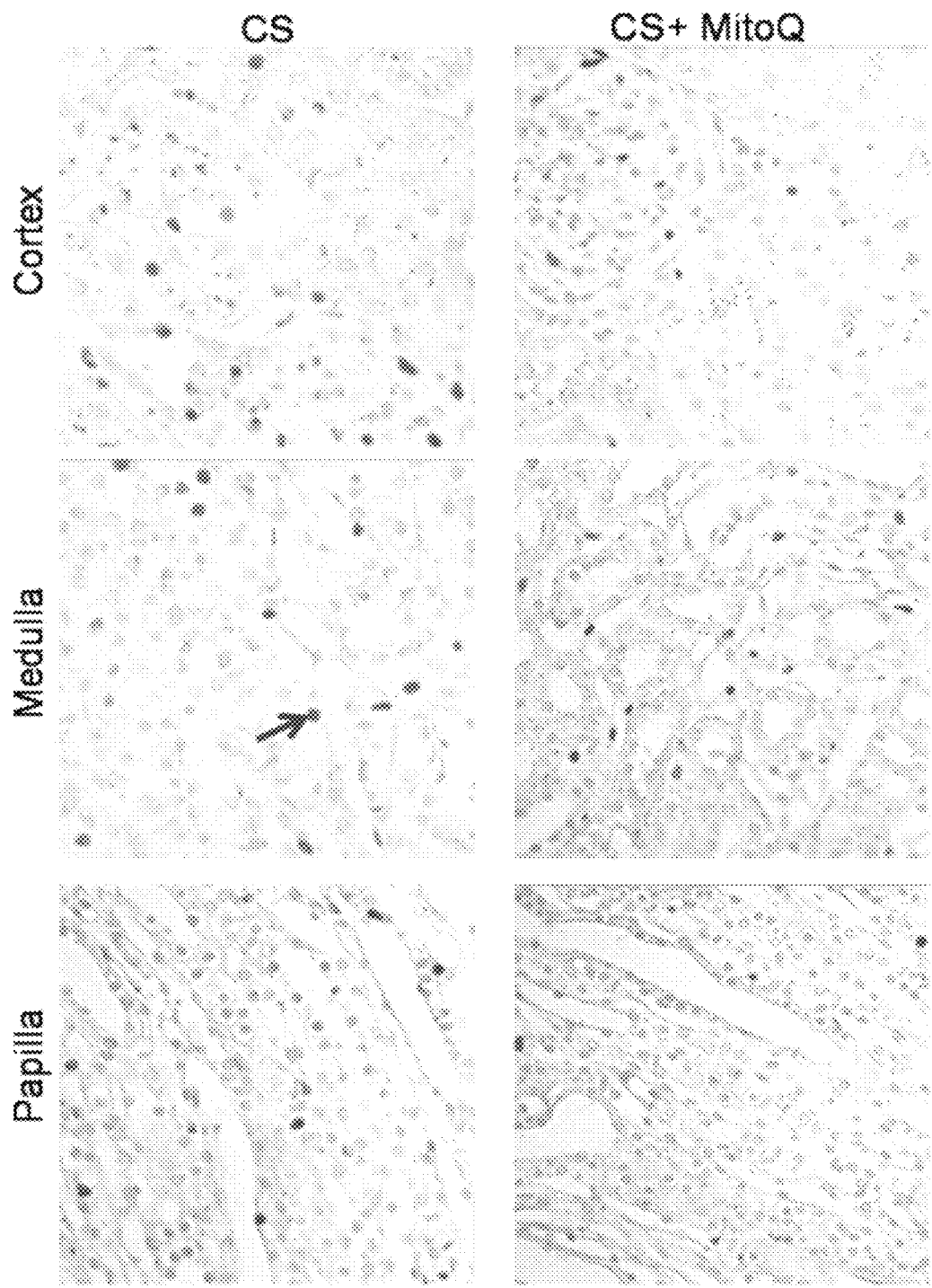
Figure 4:
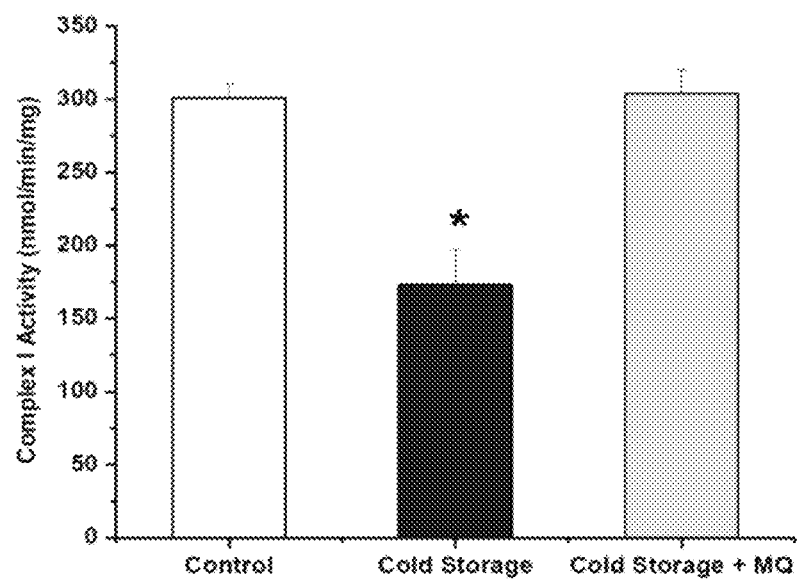
FIG. 4 depicts a graph showing the effect of MitoQ treatment (100 μM) on mitochondrial respiratory complex activity in kidneys following cold storage *P<0.05 compared with control.
Figure 5:
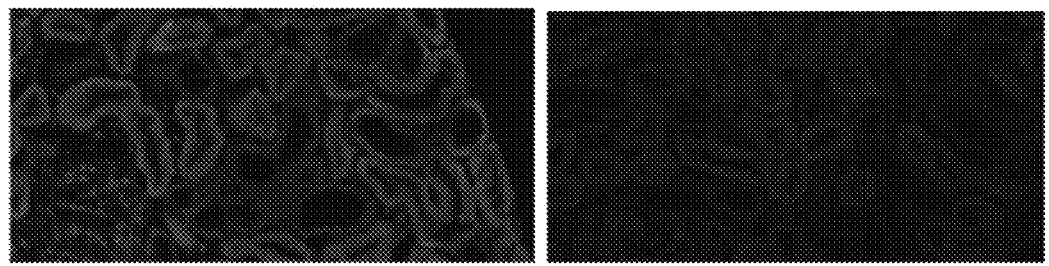
FIG. 5 depicts a photomicrograph showing that ex vivo MitoQ decreases MitoSox Red staining (superoxide). Superoxide production (using Mitosox Red) was assessed in rat kidneys exposed to cold storage (4 hr UW; 4° C.) compared to kidneys cold stored in UW+MitoQ (100 mM). n=3.
Figure 6:
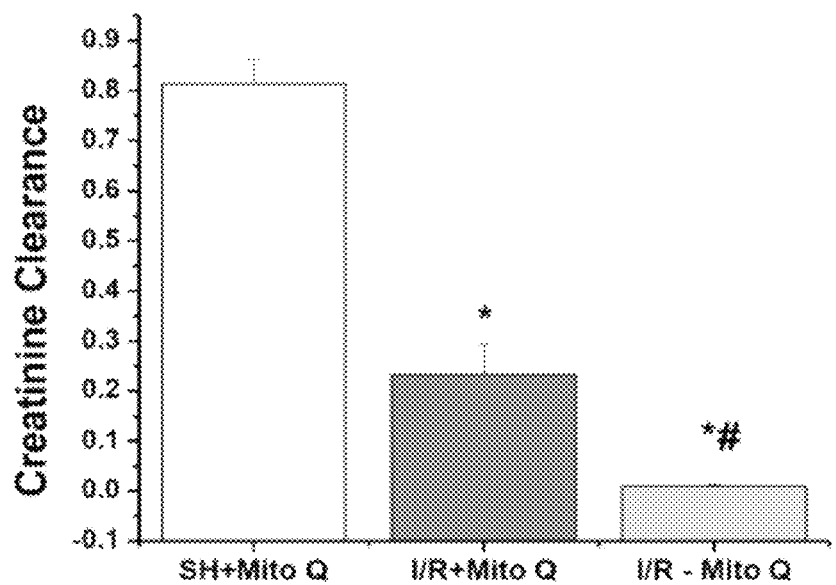
FIG. 6 depicts graphs and photomicrographs showing the effect of MitoQ treatment (48 hr oral; 100 μM) on (A) renal function (creatinine clearance), (B) MnSOD activity, (C) renal damage (PASstaining), and (D) oxidant production (nitrotyrosinestaining).
Figure 6:
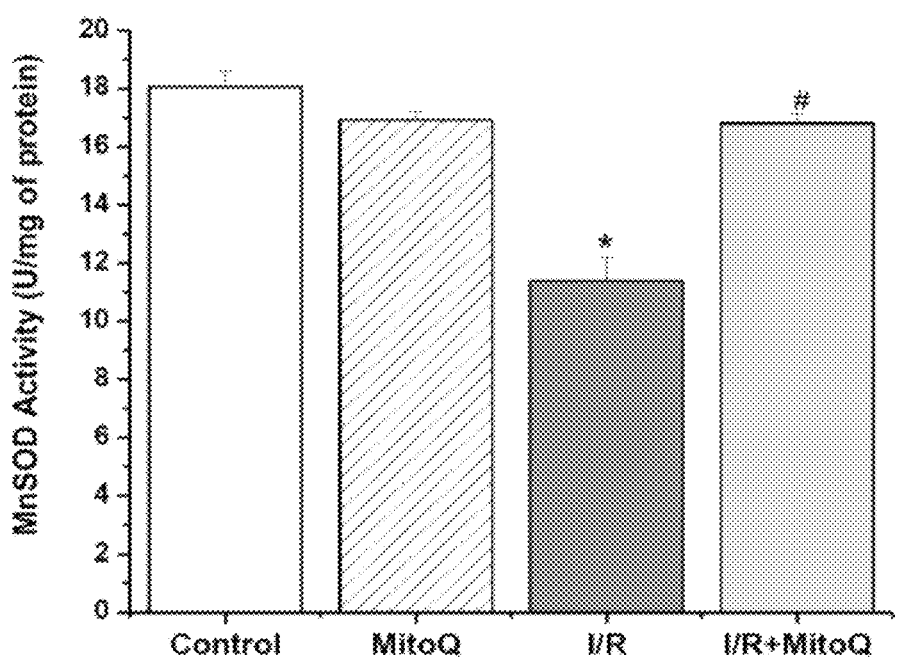
Figure 6C:
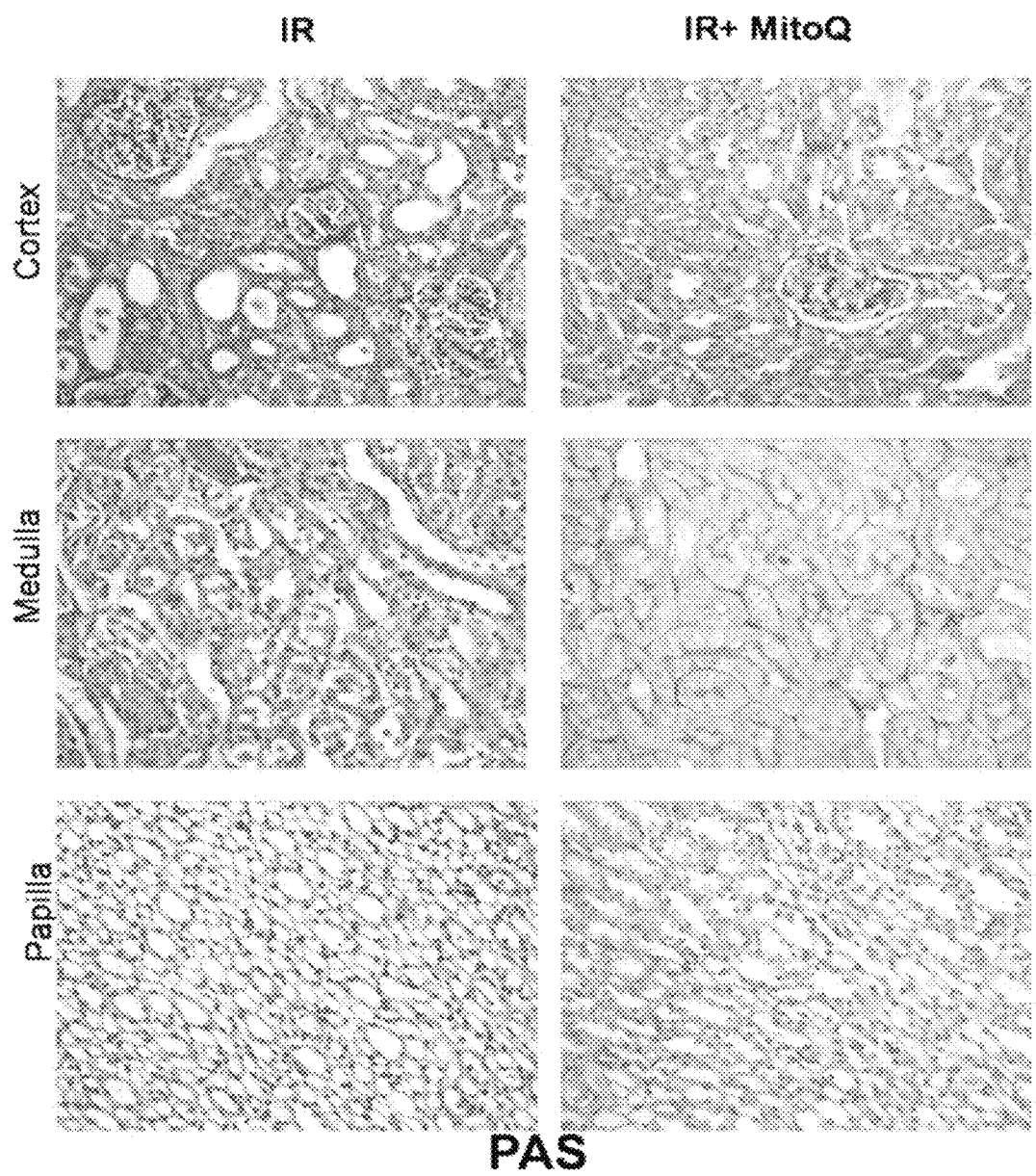
Figure 6D:
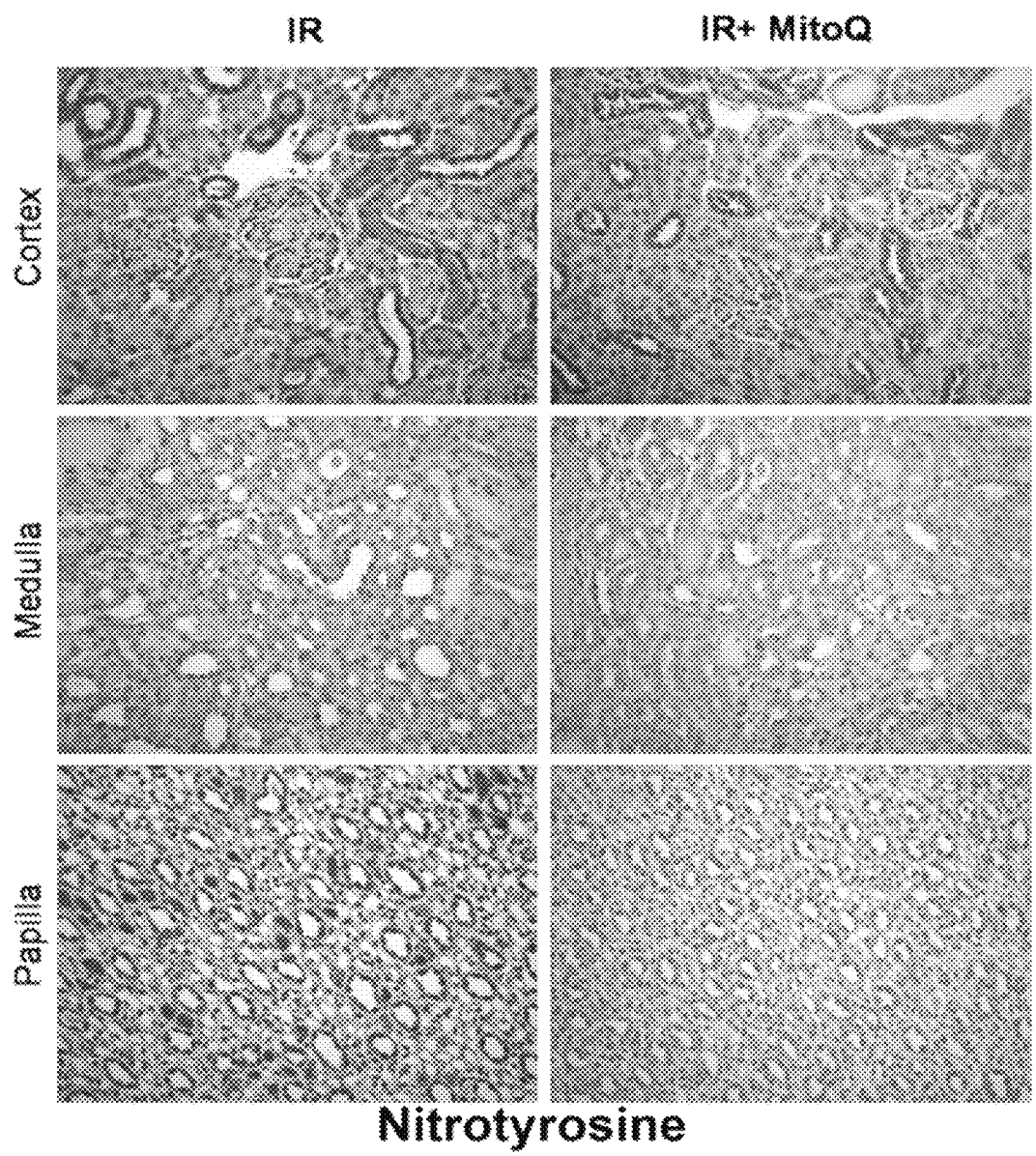
Figure 7:
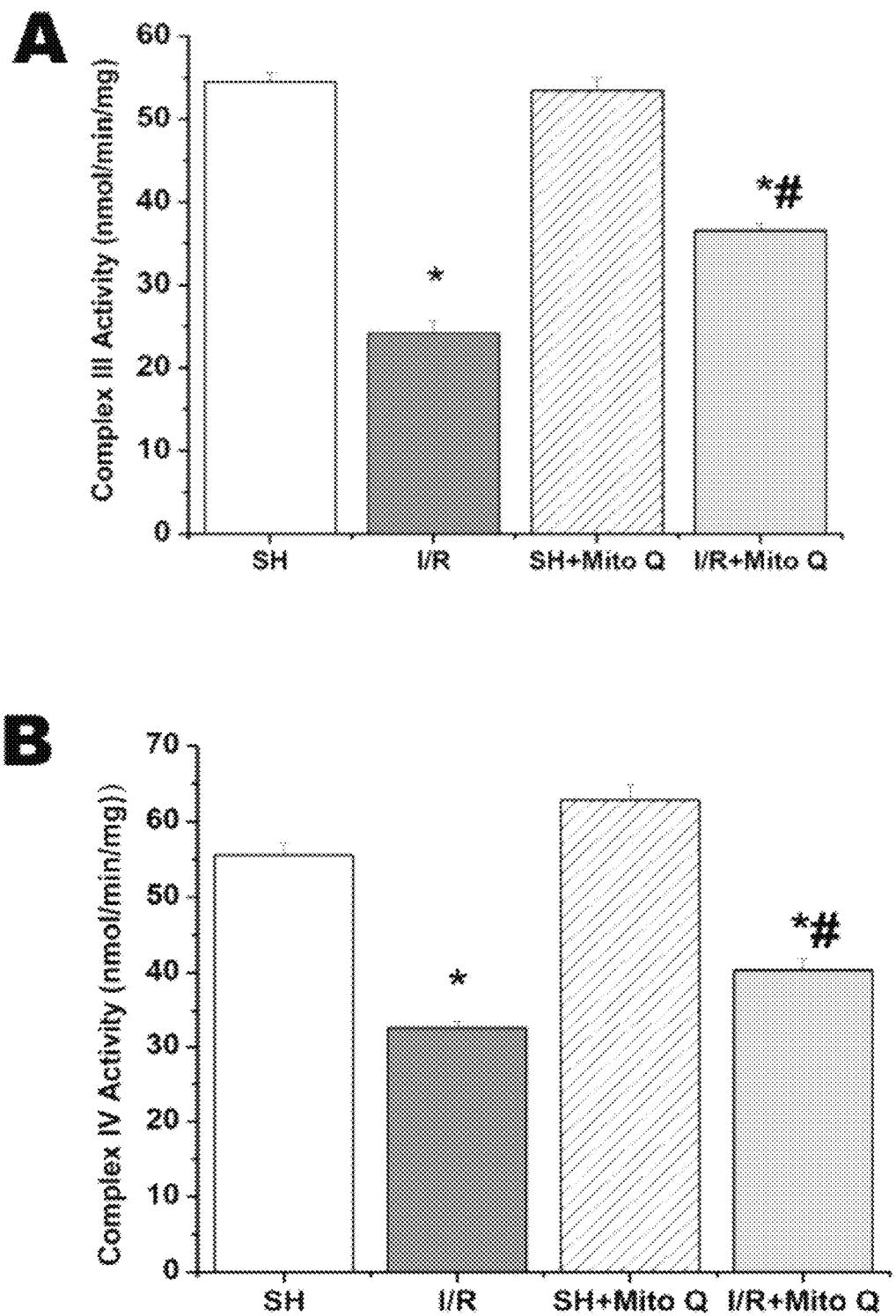
FIG. 7 depicts graphs showing the effect of MitoQ treatment (48 hr oral; 100 μM) on activity of mitochondrial respiratory complex III (A), and mitochondrial respiratory complex IV (B) in kidneys following warm I/R. *P<0.05 compared with control.

Rodent models of warm ischemia/reperfusion (I/R) (FIGS. 6-7) and cold renal preservation, as well as renal cell models of cold storage (FIG. 3-5) were used to evaluate the effectiveness of MitoQ in preventing renal damage during ischemia. The data demonstrates that MitoQ significantly reduced renal damage (histological and creatinine clearance) and improved MnSOD activity in rat kidneys following warm I/R (FIG. 6). In addition, Mito Q blunted mitochondrial superoxide production (Mitosox Red staining) and respiratory complex dysfunction following cold preservation (FIGS. 4-5).

In summary, MitoQ addition to cold preservation solutions reduces mitochondrial oxidant production, and hence renal damage, prior to transplant. This could lead to increased numbers of kidneys available for transplant (by reducing the number of discarded kidneys).

Introduction for Examples 2-6

Deceased organ donors have provided a substantial number of kidneys for patients suffering from end-stage renal disease who require transplantation. These kidneys must undergo cold preservation before transplantation. The preferred method of organ preservation in the United States is cold storage (CS), which is used in approximately 80% of transplantation cases. CS slows down metabolic reactions to preserve organ quality while allowing time for recipient selection and transport. Although this procedure is extremely valuable, CS has been shown to cause vasoconstriction, tubular and endothelial injury, and cell death, which can result in kidney discardment. Based on the 2009 Organ Procurement and Transplantation Network/Scientific Registry of Transplant Recipients Annual Report, 16% of kidneys recovered from potential deceased donors were discarded because of cold ischemia times, biopsy findings, or the inability to locate a recipient. Kidneys that are transplanted after CS, compared with kidneys from living donors, can lead to delayed graft function, chronic allograft nephropathy, graft loss, and/or increased medical cost. Because of these CS outcomes, it is imperative to determine additional strategies to enhance the quality of deceased donated kidneys during preservation.

Many research groups have made significant advances in this area by testing a range of compounds as additives to preservation solutions to improve cellular or tissue function during CS or after transplantation. Some reports suggest that the addition of bioflavonoids and trophic factor supplementation to preservation solutions should be explored further because these compounds prevented lipid peroxidation, mitochondrial dysfunction, and loss of cell viability during CS of porcine and canine renal tubular cells. The addition of polyethylene glycol and trimetazidine to preservation solutions reduced interstitial and peritubular inflammation, infiltration, and renal dysfunction of pig kidneys after cold ischemia/reperfusion (I/R). The addition of the antioxidant deferoxamine to the University of Wisconsin (UW) preservation solution has been shown to improve glomerular filtration rate and decrease cell death in a syngeneic rat kidney transplant model. Despite these efforts and other highly regarded findings, only polyethylene glycol has been reported to improve kidney preservation in a preliminary clinical study.

The examples below test whether adding mitoquinone (MitoQ), a mitochondria-targeted antioxidant, to UW preservation solution could ameliorate early CS (4 h) injury using rat renal proximal tubular cells and isolated rat kidneys. MitoQ is comprised of a ubiquinone moiety covalently linked to an aliphatic 10-carbon chain terminating with a triphenylphosphonium cation. Once localized to the mitochondria, it is reduced to the active antioxidant ubiquinol by complex II of the electron transport chain. In preventing oxidative damage, it is oxidized to ubiquinone, which is then re-reduced by complex II. MitoQ has been shown to be beneficial against oxidative stress, mitochondrial dysfunction, and cell death in cellular and animal models of sepsis, cardiac I/R, and cardiac hypertrophy. In addition, MitoQ has been tested in two phase II clinical trials where it was shown to reduce liver damage in patients with chronic hepatitis C virus infection.

MitoQ was selected because it is directly targeted to the mitochondria where it is believed the initiating events of CS injury occur. Mitochondrial reactive oxygen species (ROS; superoxide, nitric oxide, and peroxynitrite) are major contributors to mitochondrial dysfunction and oxidant production during 24-h CS and 6-h rewarming (RW) of rat renal proximal tubular cells. A control compound, decyltriphenylphosphonium bromide (DecylTPP), which has a similar chemical structure to MitoQ but without the antioxidant ubiquinol moiety, was included to determine whether the effects of MitoQ were solely caused by its antioxidative properties. The results reveal that adding MitoQ to UW preservation solution provides significant protection against oxidative stress, mitochondrial dysfunction, cell death, and renal injury during CS of rat renal proximal tubular cells and rat kidneys.

Material and Methods for Examples 2-6

Chemicals and Reagents.

Figure 8:
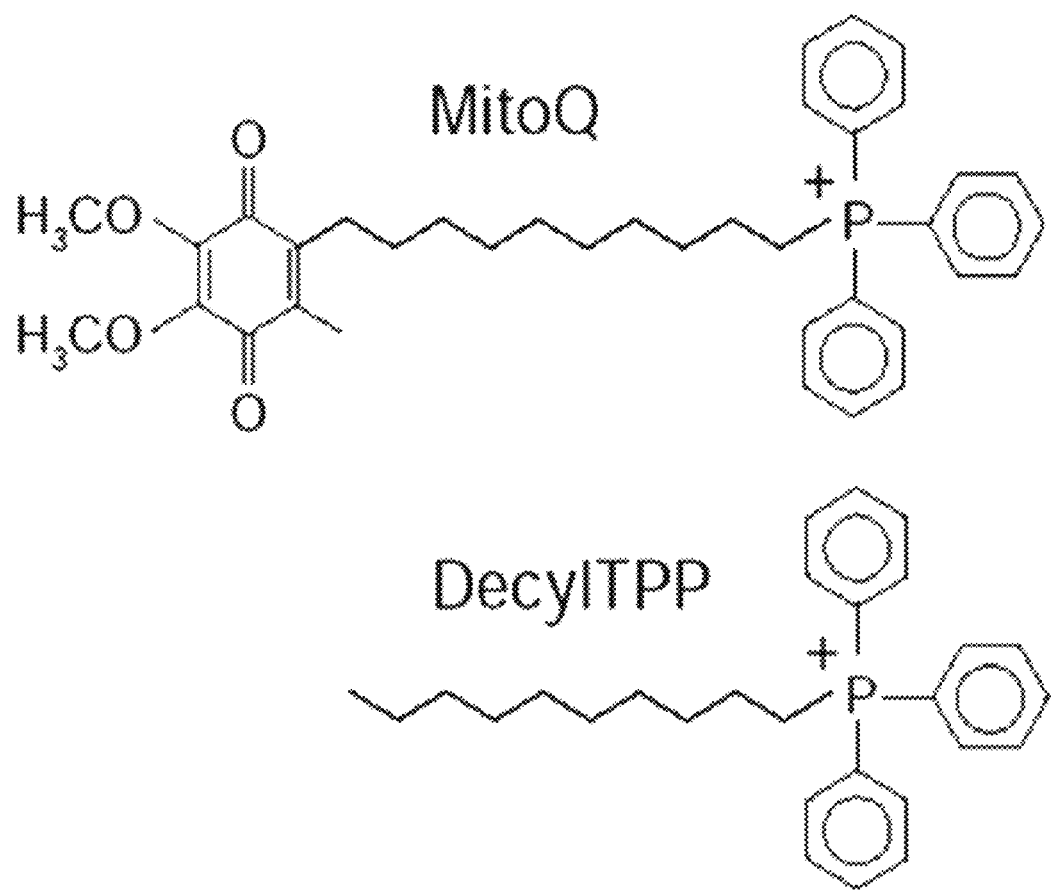
FIG. 8 depicts the chemical structures of MitoQ (top) and DecylTPP (bottom).

MitoQ mesylate and DecylTPP are shown in FIG. 8. For the in vitro experiments pure MitoQ mesylate and DecylTPP were used, whereas MitoQ mesylate bound to cyclodextrin and DecylTPP were used for the ex vivo studies. MitoQ mesylate was bound to cyclodextrin to make MitoQ easier to handle.

Cold Storage In Vitro Model.

Normal rat kidney proximal tubular cells (NRK-52E; American Type Culture Collection, Manassas, Va.) were maintained in six-well 100 or 150-mm, or 150-mm plates in a humidified incubator gassed with 5% $CO_2$ and 95% air at 37° C. in DMEM (Invitrogen, Carlsbad, Calif.) containing 5% fetal calf serum (FCS). Cells were grown to 60% confluence and divided into four treatment groups: 1) untreated (Untx), 2) CS, 3) CS+MitoQ, and 4) CS+DecylTPP. Untreated cells remained at 37° C. in DMEM containing 5% FCS (group 1). CS was initiated by washing cells with cold PBS (Invitrogen) twice and storing them in UW/Viaspan solution alone (4 h at 4° C.) (group 2), CS+MitoQ (1 µM) (group 3), or CS+DecylTPP (1 µM) (group 4). In separate experiments, cells were exposed to CS plus RW by replacing UW solution alone or UW solution containing MitoQ or DecylTPP with DMEM containing 5% FCS overnight (18 h at 37° C.).

Cold Storage Ex Vivo Model.

All animals were treated according to the National Institutes of Health Guide for the Care and Use of Laboratory Animals and the University of Arkansas for Medical Sciences Institutional Animal Care and Use Committee guidelines. Male Fischer 344 inbred rats (Charles Rivers Laboratories, Inc., Wilmington, Mass.) weighing between 250 and 300 g were anesthetized with ethrane, followed by shaving and prepping with betadine. A 2-ml bolus of 0.9% (w/v) NaCl was administered intravenously, and an incision was made 1 cm superior to the symphysis pubis to the tip of the xiphoid process. Bulldog clamps were placed on the aorta and vena cava (proximal and distal to the renal vessels) to prevent blood flow to the kidneys. A 22-gauge surgical needle was used to puncture the rat's aorta to flush the renal grafts with saline (10 ml per kidney) using a small catheter. Once the kidneys started to turn light brown (perfusion), another vent was formed in the vena cava to allow blood flow from the kidneys. Once both kidneys were completely flushed, the right kidney was recovered and served as a control (group 1), and the left kidney was exposed to CS alone for 4 h at 4° C. (group 2). In additional experiments, kidneys were flushed with saline through the aorta using a small catheter followed by flushing the right kidney with saline containing MitoQ (100 µM) and the left kidney with saline containing DecylTPP (100 µM) (10 ml per kidney). Tissues were recovered and stored in CS+MitoQ (100 µM; right kidney) or CS+DecylTPP (100 µM; left kidney) for 4 h at 4° C. (groups 3 and 4, respectively). A thin middle section from all of the kidneys were cut and immediately fixed in 10% formalin before being embedded in paraffin for sectioning (4 µm) and histological evaluation. The remaining portion of the kidneys were quickly frozen in liquid nitrogen and stored in −80° C. until needed for biochemistry analyses.

Mitochondrial Superoxide Production.

MitoSOX Red (Invitrogen) was used to measure mitochondrial superoxide generation during CS. In brief, cells were preloaded in the dark with MitoSOX red (5 µM; 10 min at 37° C.) before treatment (groups 1-4). Fluorescence was visualized using an Eclipse E800 microscope (Nikon, Melville, N.Y.) with a rhodamine filter using a water immersion objective (60×). Fluorescent images of NRK cells were captured with equal exposure times and quantified by averaging the mean intensity fluorescence of five random cells in three different fields using Nikon N is Elements software. In separate experiments, cells were grown on coverslips, preloaded with MitoSOX Red before treatment (groups 1-4), and evaluated for mitochondrial superoxide generation using a Hitachi F-2500 spectrofluorometer (Hitachi, Tokyo, Japan) equipped with a coverslip holder using two different excitation wavelengths: 396 and 510 nm with the emission measured at 580 nm as previously described. In addition, rat kidneys were monitored for mitochondrial superoxide generation by flushing kidneys with saline through the aorta using a small catheter as described under Cold Storage Ex Vivo Model, followed by saline containing MitoSOX Red (5 µM; 10 ml/kidney) before treatment (groups 1-4). Paraffin sections were analyzed using the rhodamine filter on the Nikon Eclipse 800 microscope (20×).

Nitrotyrosine Immunocytochemistry and Immunohistochemistry.

NRK cells (groups 1-4) were assessed for nitrotyrosine formation as previously described. In brief, cells were immunostained with nitrotyrosine polyclonal antibody (1:200; Millipore, Billerica, Mass.), Alexa-594-conjugated antibody (1:1000; Invitrogen), and 4',6-diamidino-2-phenylindole (1:100; Invitrogen) for nuclear counterstaining. Positive controls were cells treated with peroxynitrite (0.8 mM) in PBS for 5 min at room temperature. Negative controls were cells treated with peroxynitrite, but the antibody binding specificity was confirmed by blocking the nitrotyrosine antibody with excess 3-nitrotyrosine (10 mM; Sigma-Aldrich, St. Louis, Mo.). Nitrotyrosine staining was evaluated and captured with equal exposure times using a Nikon Eclipse 800 microscope (40×oil). Images were quantified by averaging the mean intensity fluorescence of five random cells in three different fields using Nikon N is Elements software. Renal tissue sections were assessed for the presence of nitrotyrosine protein adducts by nitrotyrosine immunohistochemistry. Tissue sections were deparaffinized and rehydrated, followed by antigen retrieval (20-min incubation at 95° C. with 10 mM sodium citrate buffer, pH 6.0; Sigma-Aldrich). Sections were blocked with peroxidase suppressor (Thermo Scientific, Rockford, Ill.) and DAKO protein block (Dako North America, Inc., Carpinteria, Calif.) and incubated overnight at 4° C. with the polyclonal rabbit antinitrotyrosine antibody (1:3000). Sections were developed using the DAKO LSAB+ System-HRP kit (Dako North America, Inc.) followed by Mayer's hematoxylin counterstaining (Electron Microscopy Sciences, Hatfield, Pa.), dehydration, and mounting with Cytoseal-60 (Electron Microscopy Sciences). The specificity of nitrotyrosine antibody binding in the renal tissue was confirmed by blocking the antibody with 3-nitrotyrosine (10 mM).

Mitochondrial Respiratory Complex Activity.

NRK cell and rat kidney mitochondria were isolated by centrifugation on a sucrose density gradient. The activity of mitochondrial respiratory complexes I, II, III, or IV were assayed spectrophotometrically using 100 µg of mitochondrial protein at 30° C. as previously described.

Morphological Assessments.

Renal sections were assessed for tissue injury using the periodic acid-Schiff reaction. Tissues were deparaffinized and rehydrated, followed by oxidation with 0.5% periodic acid solution (Sigma-Aldrich) for 5 min at room temperature. Sections were rinsed with distilled water and incubated with Schiff reagent (Sigma-Aldrich) for 15 min at room temperature. Subsequently, sections were washed with tap water, counterstained with Mayer's hematoxylin, dehydrated, and mounted with Cytoseal-60. Morphological evaluation of tubular dilation, brush border loss, and cellular debris/tubular cast formation were performed blindly with light microscopy and assessed semiquantitatively according to the following scoring system: 0, no changes; 1, mild changes; 2, moderate changes, and 3, severe changes.

Cell Death Measurement.

Cell cytotoxicity was determined using the LDH-Cytotoxicity Assay Kit II (Biovision Research Products, Mountain View, Calif.) according to the manufacturer's instructions. Absorbance was measured at 450 nm using a SpectraMax 190 microplate reader and SpectraMax software (Molecular Devices, Sunnyvale, Calif.). Renal cell death was determined using TUNEL staining. Kidney sections were deparaffinized, rehydrated, and exposed to antigen retrieval (20-min incubation at 95° C. with 10 mM sodium citrate buffer, pH 6.0) followed by washing with distilled water and quenching of endogenous peroxidase. Sections were immersed in TdT labeling buffer and then incubated in a humidified chamber with the labeling reaction mix from the TAGS 2 TdT-DAB In Situ Apoptosis Detection kit (Trevigen, Inc., Gaithersburg, Md.) for 1 h at room temperature. The reaction was stopped with TdT stop buffer, and slides were subsequently washed with PBS. Sections were incubated for 10 min with streptavidin-HRP followed by development with diaminobenzidine solution, counterstaining with Mayer's hematoxylin, dehydration, and mounting with Cytoseal-60. The amount of cell death was calculated by averaging the number of cells positive for TUNEL (brown staining) in 10 different fields (cortex and medulla) (20×). All images were taken at equal exposure times (40×oil).

Statistical Analysis.

Results are presented as mean±S.E.M. Means were obtained from three (in vitro) or five (ex vivo) independent experiments. One-way analysis of variance was used to compare the mean values among the untreated/controls and treatment groups, followed by Tukey's test to compare differences in mean between two groups at 95% level of confidence using Origin 6.0 statistical software (OriginLab, Northampton, Mass.). Differences with a P value less than 0.05 was considered statistically significant.

Example 2

Protective Effect of MitoQ on Mitochondrial Superoxide Generation During CS

Figure 9A:
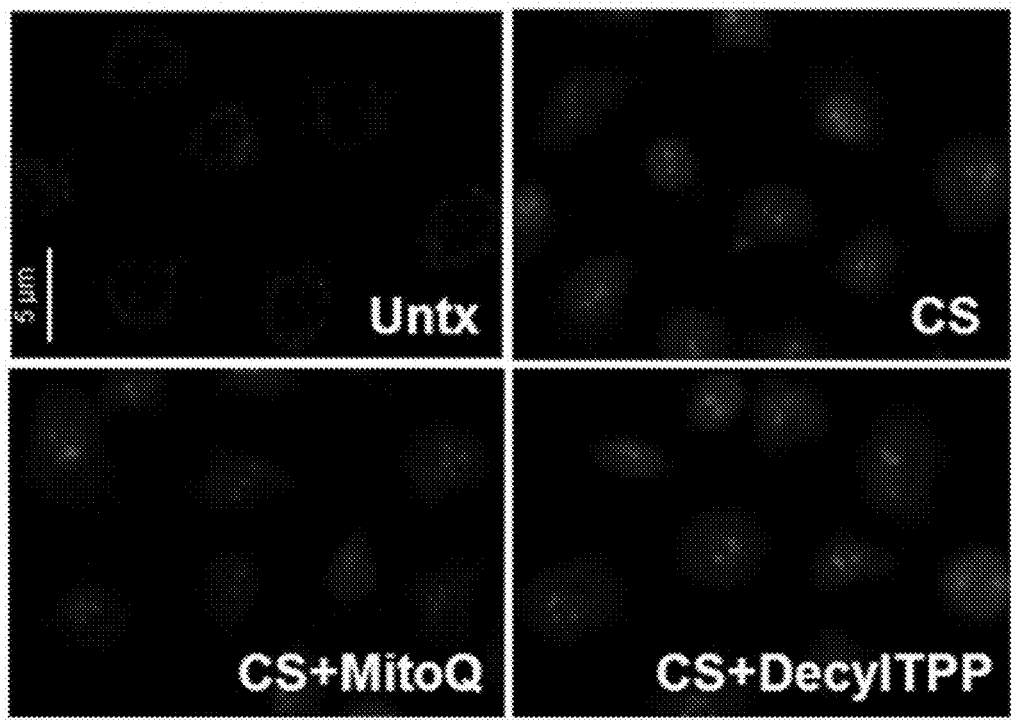
FIG. 9 depicts fluorescence microscope images and plots depicting the effect of MitoQ on mitochondrial superoxide generation during CS. MitoSOX Red (5 μM for 10 min) was used to assess mitochondrial superoxide levels. (A) fluorescence microscopic images of untreated (Untx) cells and cells exposed to CS (top) and cells exposed to CS+MitoQ (1 μM) and CS+DecylTPP (1 μM) (bottom) (60×). Results are representative of three experiments using different cell cultures. (B) MitoSOX Red staining was quantified using the N is Elements software. Values are expressed as mean±S.E.M. (n=3). , P<0.01 compared with Untx cells; †, P<0.05 compared with CS cells. (C) fluorescence spectrometry of NRK cells grown on coverslips and tested for fluorescence of MitoSOX Red at wavelengths of 396- and (D) 510-nm excitation/ 580-nm emission. Values are expressed as mean fold changes in arbitrary fluorescence units over Untx cells±S.E.M. (n=3). , P<0.01 compared with Untx cells; †, P<0.05 compared with CS cells. (E) fluorescence photomicrographs of rat kidneys flushed with MitoSOX Red (left to right): control, CS, CS+MitoQ (100 μM), and CS+DecylTPP (100 μM) (20×). Results are representative of five animal experiments.
Figure 9:
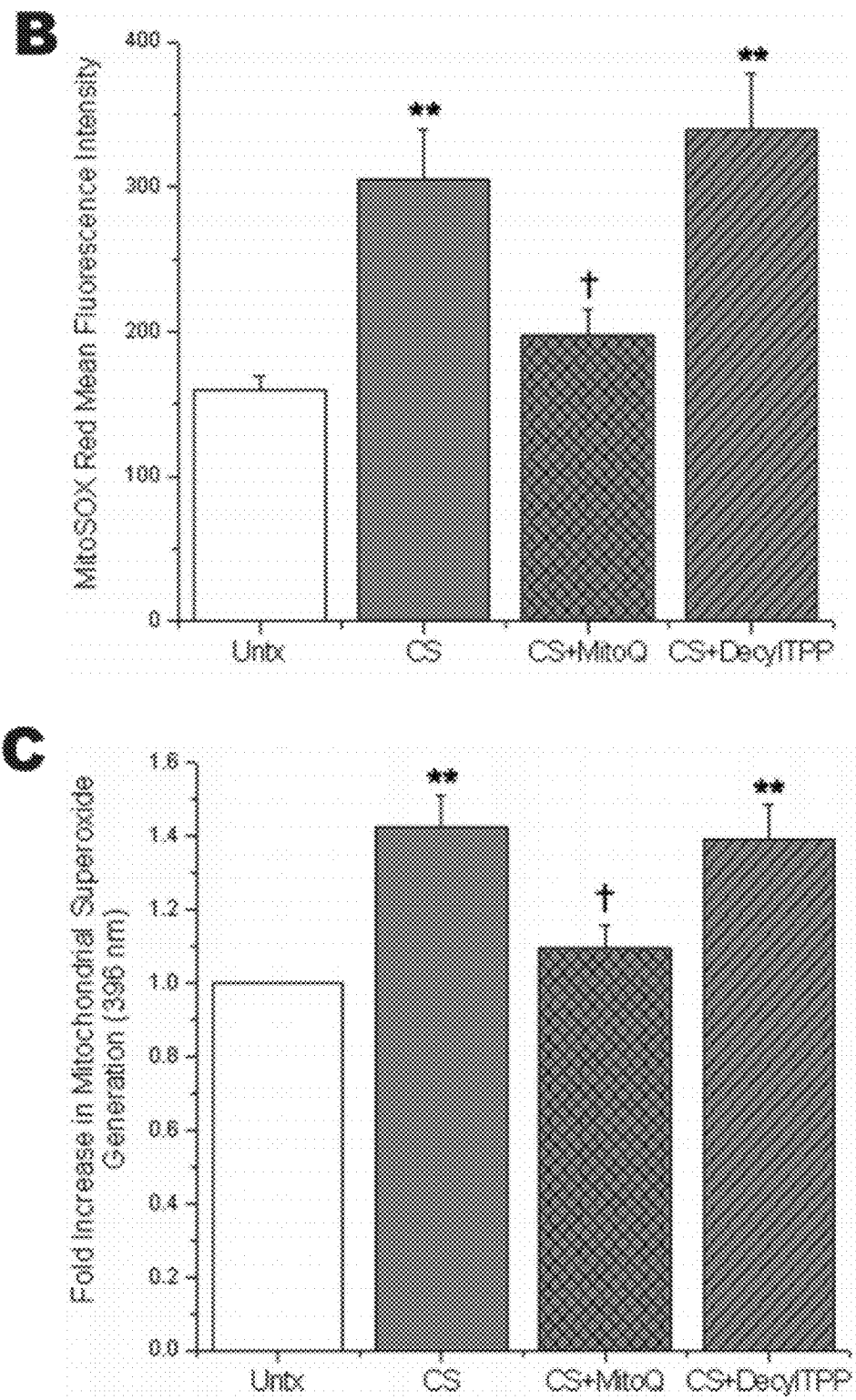
Figure 9D:
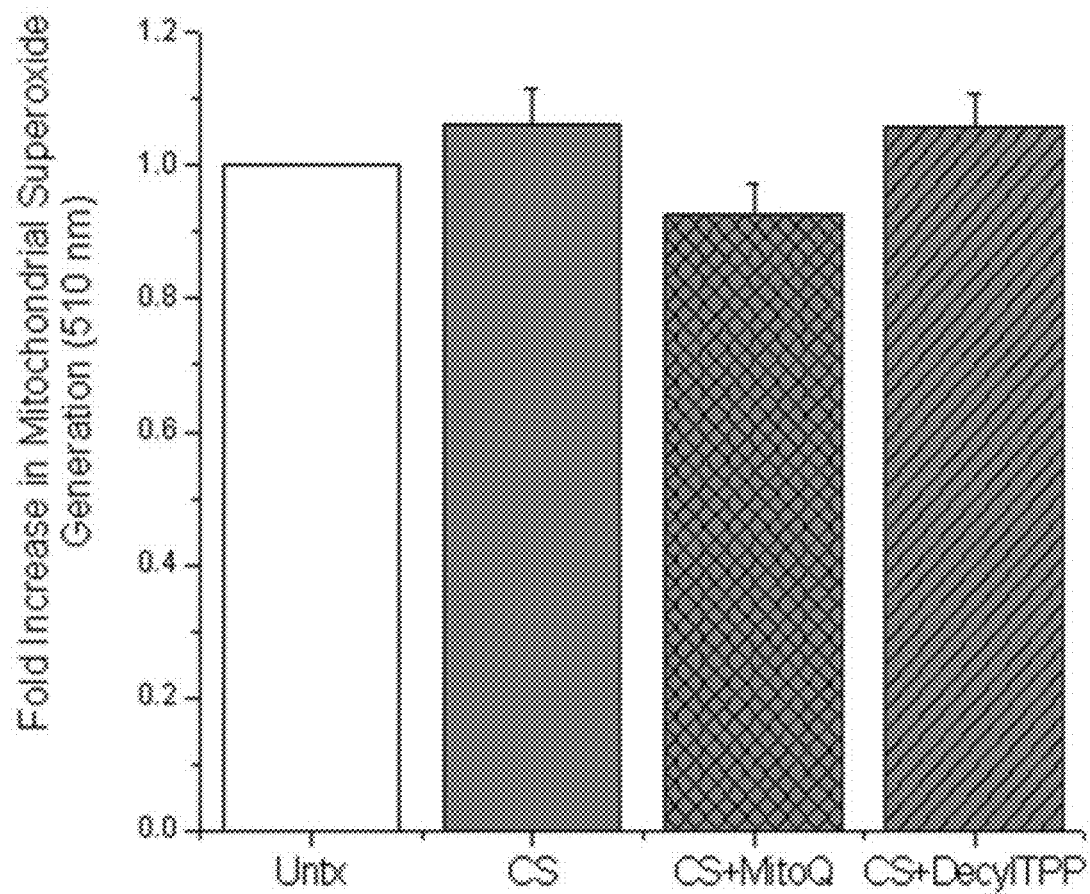
Figure 9E:
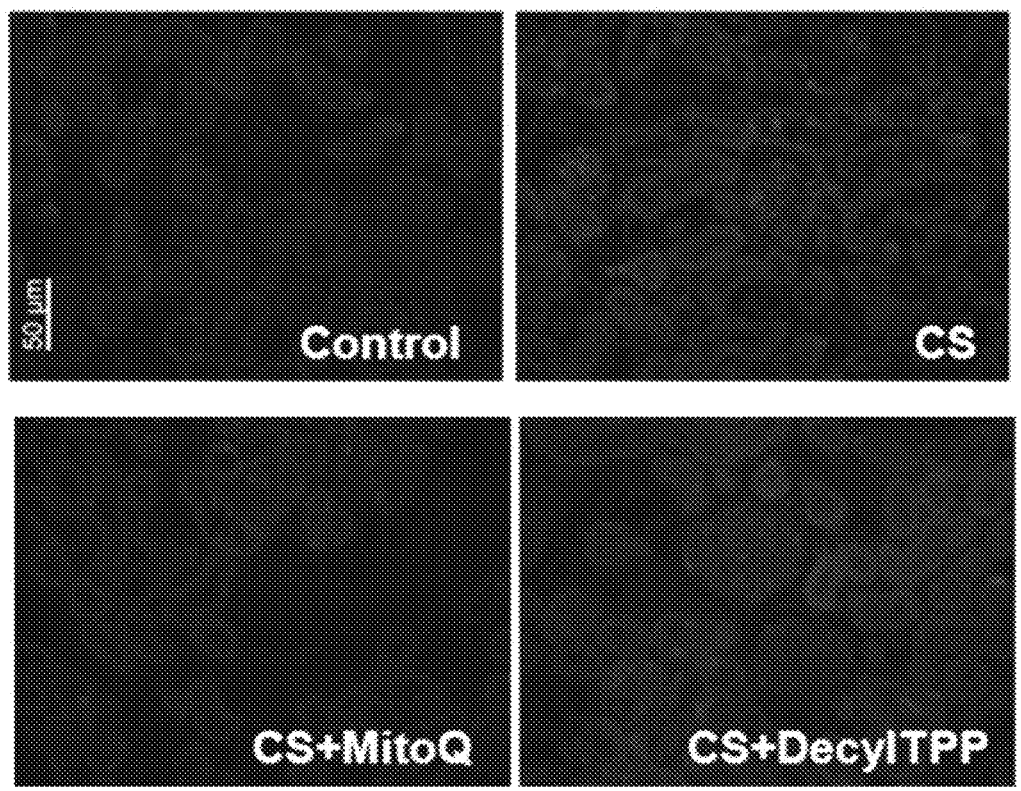

The optimal doses for MitoQ and DecylTPP treatment were selected from dose-response experiments during 4-h CS. For the cellular-based studies, 1 µM was chosen from a range of 0.5, 0.75, 1.0, 1.5, and 2 µM, whereas the most efficacious dose for the ex vivo studies was 100 µM from a dose-response study of 50, 100, and 500 µM (data not shown). The potential protective benefits of MitoQ treatment against CS injury were tested initially using MitoSOX Red, a mitochondrial-targeted fluorescent dye that measures mitochondrial superoxide generation. As shown in FIGS. 9A and B, NRK cells exposed to CS resulted in a ~2-fold increase in fluorescence due to mitochondrial superoxide compared with untreated cells. MitoQ offered significant protection against CS-induced mitochondrial superoxide generation; whereas the control compound DecylTPP did not offer any protection. This was further confirmed using a spectrofluorometric-based assay detecting MitoSOX Red fluorescence excitation at 396 and 510 nm, where 396 nm is a specific indicator of mitochondrial superoxide, and 510 nm detects nonspecific oxidant generation (FIGS. 9C and D). In addition, kidneys exposed to CS alone displayed increased mitochondrial superoxide generation compared with control kidneys (FIG. 9E). MitoQ treatment markedly decreased mitochondrial superoxide generation, whereas kidneys treated with DecylTPP had comparable levels of mitochondrial superoxide to kidneys exposed to CS alone (FIG. 9E).

Example 3

MitoQ Attenuates Nitrotyrosine Adduct Formation During CS

Figure 10A:
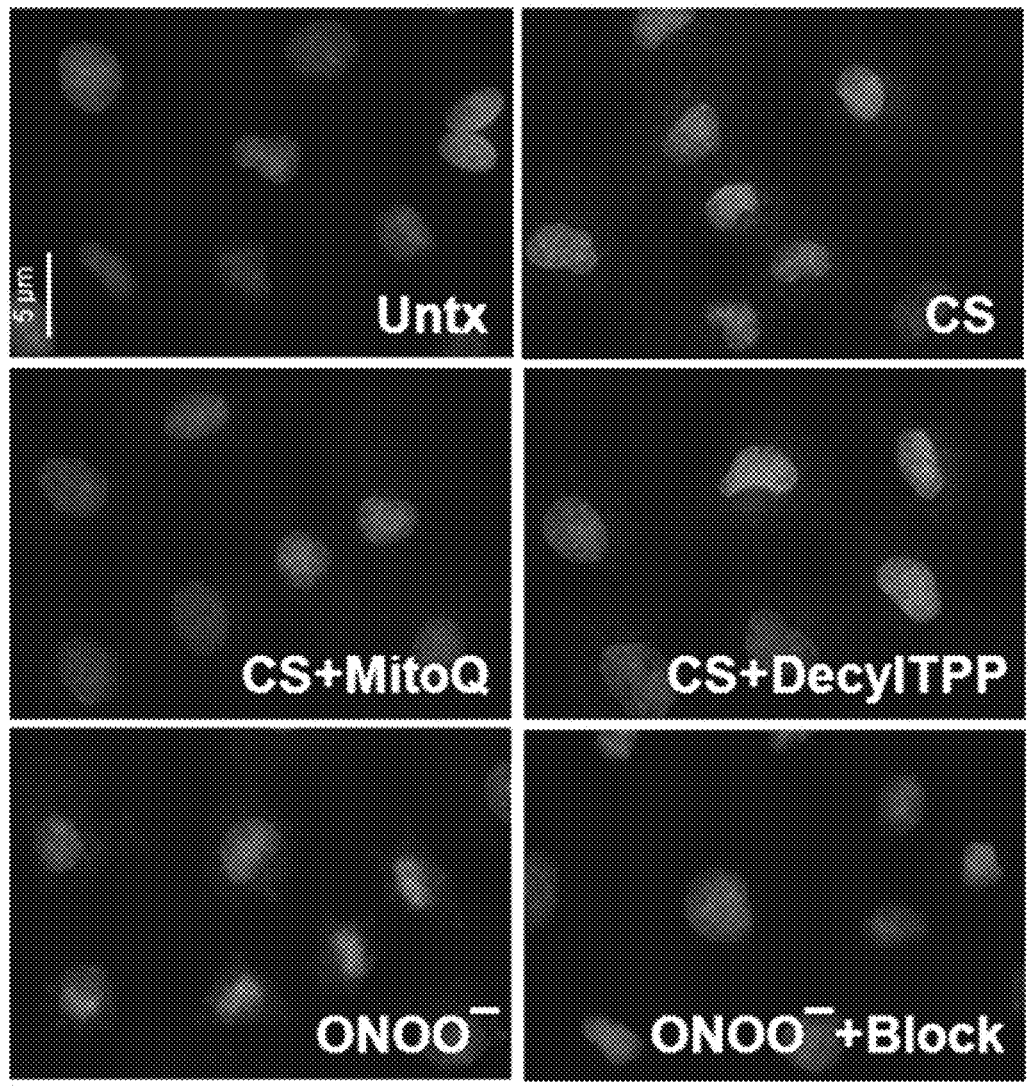
FIG. 10 depicts photomicrographs and a plot depicting MitoQ attenuation of nitrotyrosine formation during CS. Cells were immunostained with nitrotyrosine polyclonal antibody (1:200), Alexa-594-conjugated antibody (1:1000), and 4',6-diamidino-2-phenylindole (1:100) for nuclear counterstaining. Cells positive for nitrotyrosine fluoresce red. (A) fluorescence microscopic images of untreated (Untx) cells and cells exposed to CS (top), and cells exposed to CS+MitoQ (1 μM) and CS+DecylTPP (1 μM) (middle). Bottom, the images represent staining controls: NRK cells treated with peroxynitrite (ONOO—; positive control) and NRK cells treated with ONOO— but preincubated with excess 3-nitrotyrosine (ONOO—+block; negative control) (40× oil). Results are representative of three experiments using different cell cultures. (B) Nitrotyrosine staining was quantified using the N is Elements software. Values are expressed as mean±S.E.M. (n=3). *, P<0.05 or ***, P<0.001 compared with Untx cells; †, P<0.05 compared with CS cells. (C) photomicrographs of nitrotyrosine immunohistochemistry of rat kidneys: control and CS (top), kidneys exposed to CS+MitoQ (100 μM) and CS+DecylTPP (100 μM) (middle), and CS+block (CS kidney+10 mM 3-nitrotyrosine) (bottom) (20×). Results are representative of five animal experiments.
Figure 10B:
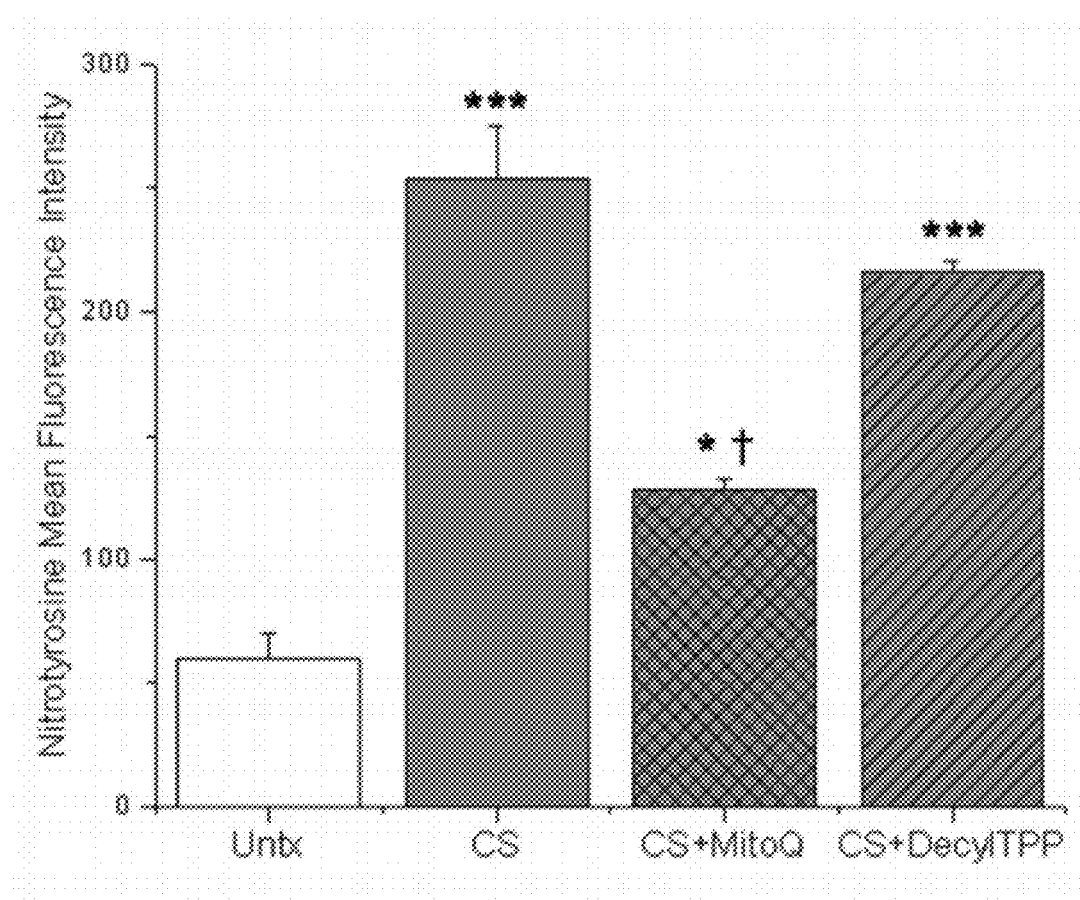
Figure 10C:
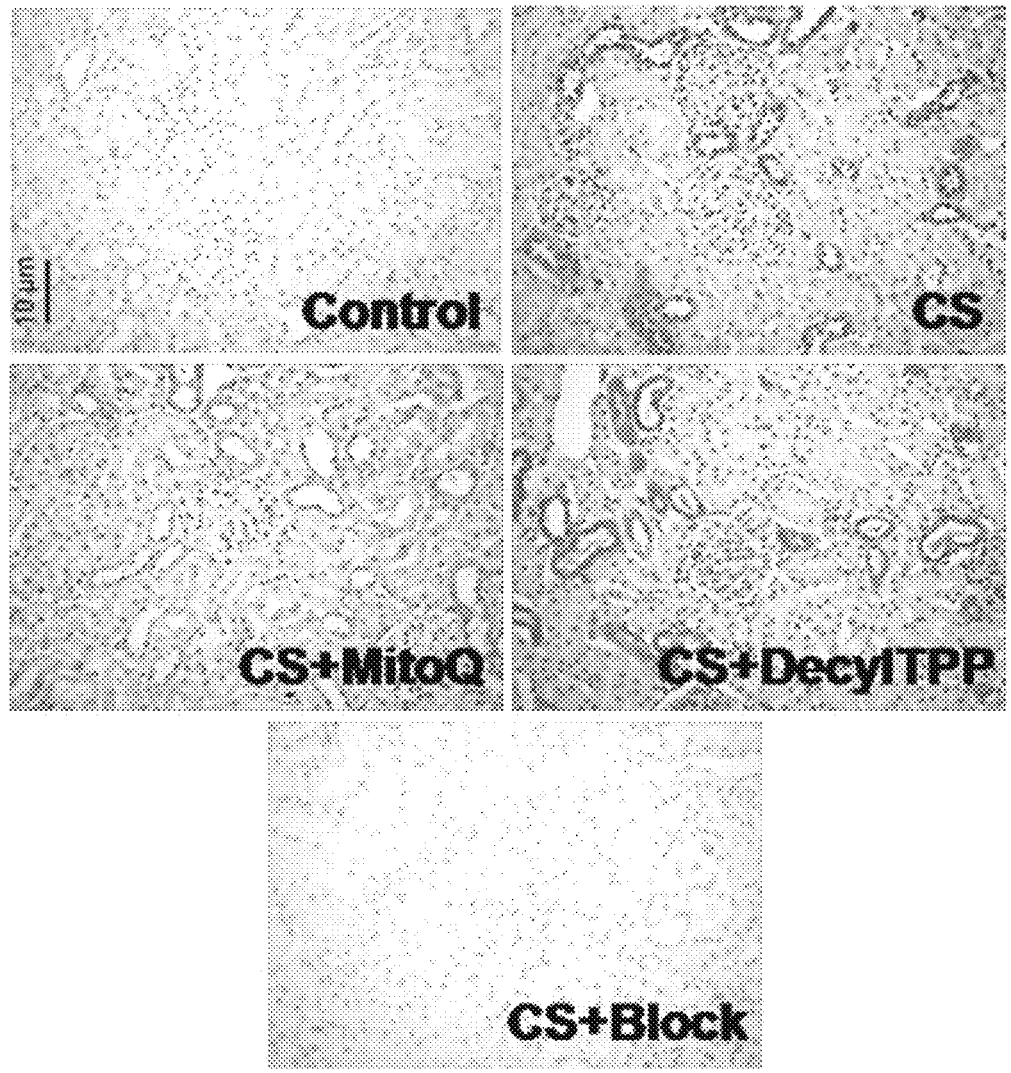

Immunocytochemistry and immunohistochemistry were used to evaluate nitrotyrosine protein adducts during CS. As shown in FIGS. 10A and B, NRK cells exposed to CS alone had a significant increase in nitrotyrosine staining (red fluorescence) compared with untreated cells. MitoQ attenuated nitrotyrosine formation ~2-fold, whereas the control compound DecylTPP did not decrease CS-mediated nitrotyrosine formation (FIGS. 10A and B). Peroxynitrite-treated cells had intense nitrotyrosine formation (positive control) and was blocked when the nitrotyrosine antibody was preabsorbed with excess 3-nitrotyrosine (negative control; $ONOO^-$+ block). Rat kidney immunohistochemistry data were consistent with the in vitro study findings regarding the effect of MitoQ and nitrotyrosine. FIG. 10C shows an increase in nitrotyrosine (brown staining) in the distal and proximal tubules and to a lesser extent in the glomeruli of CS kidneys compared with control kidneys. Kidneys treated with MitoQ had less nitrotyrosine formation. In contrast, DecylTPP-treated kidneys had similar amounts of nitrotyrosine compared with CS kidneys. The specificity of nitrotyrosine staining was also confirmed using antibody preabsorbed with excess 3-nitrotyrosine (CS+block).

Example 4

MitoQ Prevents Mitochondrial Respiratory Complex Inactivation During CS

Figure 11:
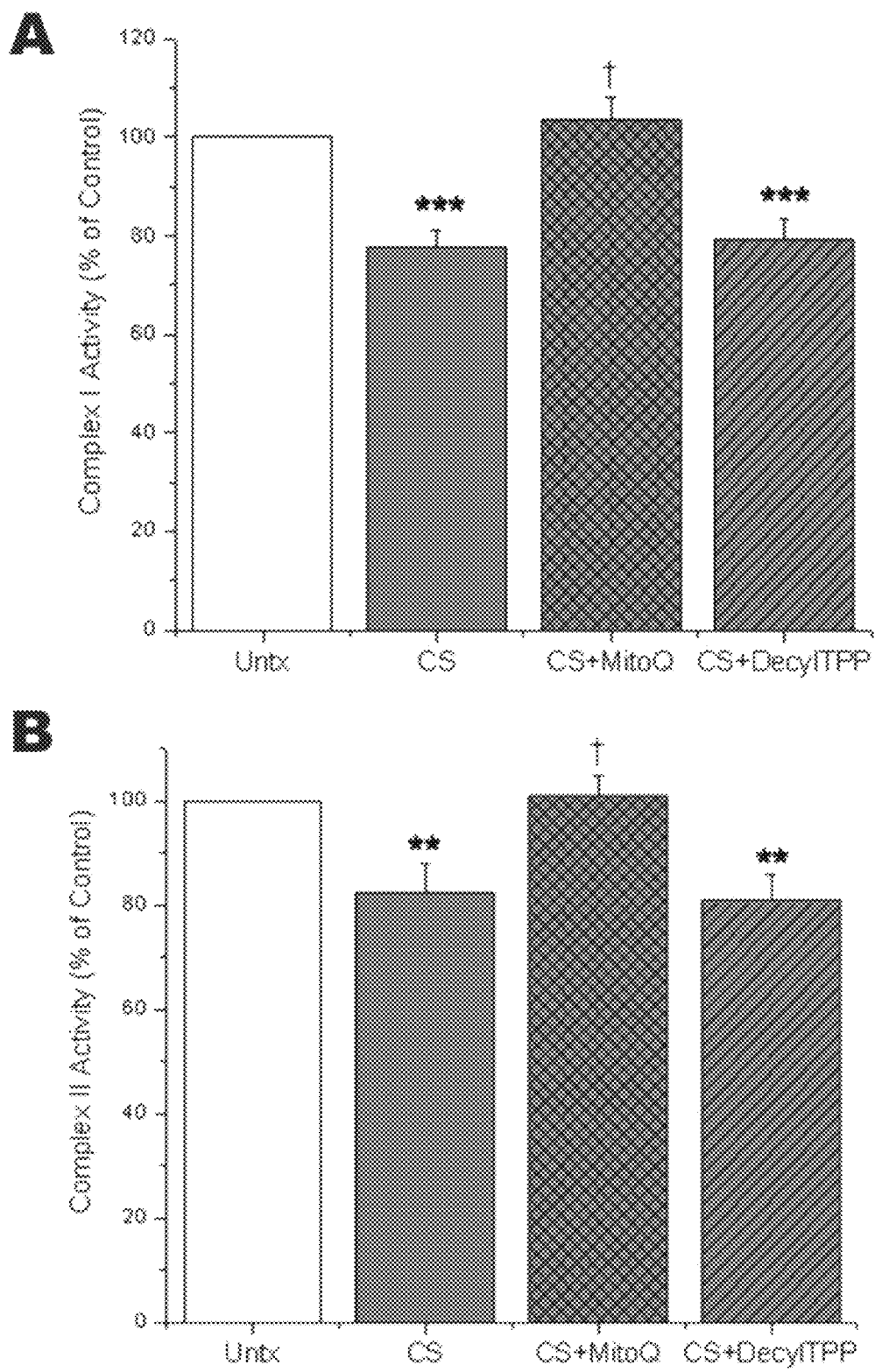
FIG. 11 depicts graphs showing that MitoQ prevents mitochondrial respiratory complex inactivation during CS. Individual mitochondrial respiratory complex activities were measured using isolated mitochondria from NRK cells (A and B) and isolated rat kidney mitochondria (C-F) exposed to CS, CS+MitoQ, or CS+DecylTPP (1 μM in vitro and 100 μM ex vivo). Values are expressed as percentage mean±S.E.M. (n=3 in vitro or 5 ex vivo) of respective controls (set to 100). , P<0.01 or *, P<0.001 compared with respective controls. †, P<0.05 compared with CS.
Figure 11:
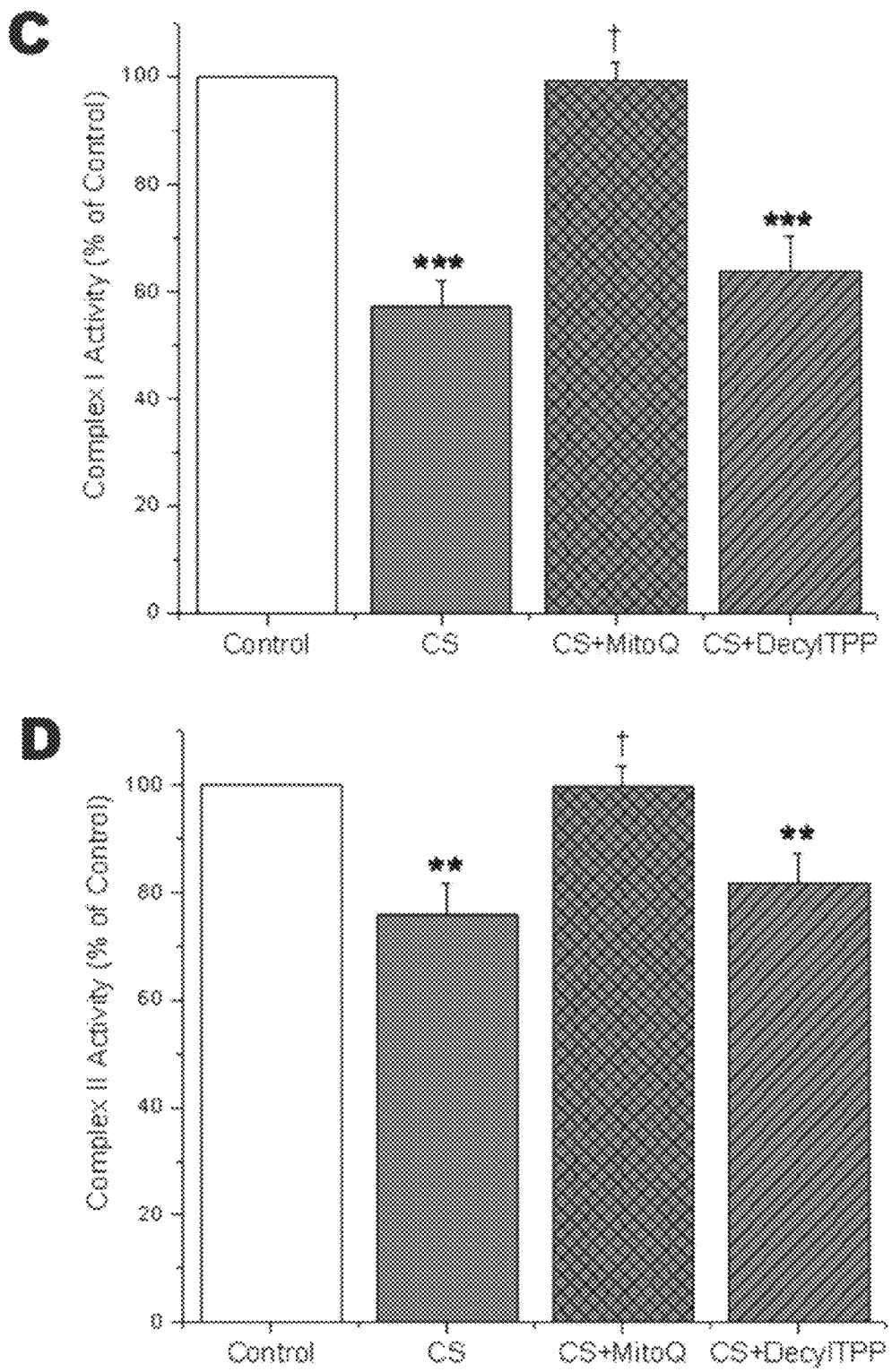
Figure 11:
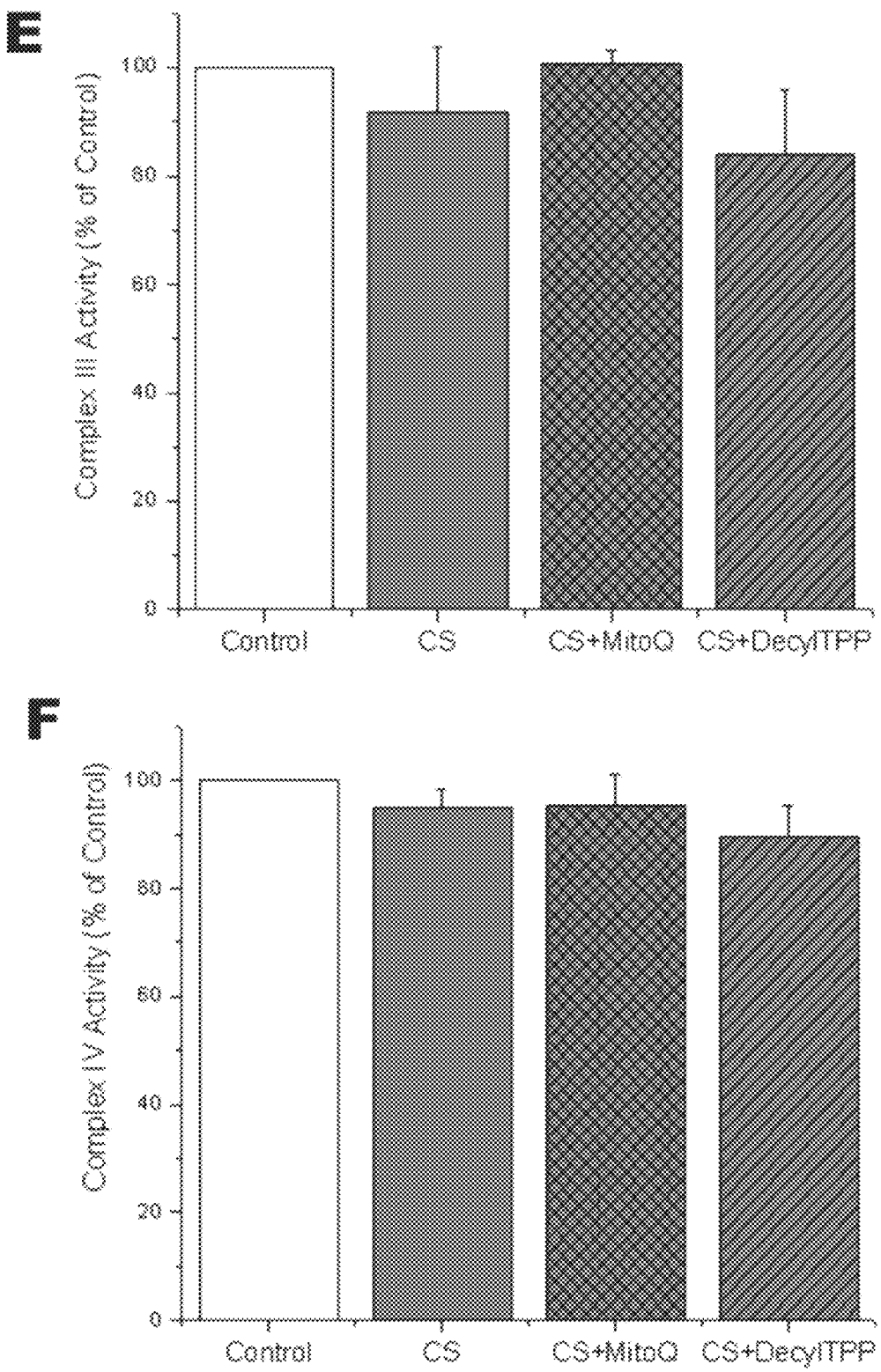

Mitochondrial respiratory complex activity was evaluated in both the in vitro and ex vivo renal models to investigate whether 4-h CS alters mitochondrial respiratory function. Complexes I and II were significantly inactivated after CS of NRK cells compared with untreated cells (FIG. 11). MitoQ completely prevented complex I and II inactivation, whereas DecylTPP had no significant effect on complex activity. Complexes III and IV were not assessed in this study because it was previously shown that both complex activities are unchanged with 24-h CS; therefore evaluation of these complex activities was not warranted. Consistent with the in vitro findings, CS of rat kidneys led to partial inactivation of complexes I and II activity and had no effect on complexes III and IV (FIG. 11). MitoQ protected against complex I and II inactivation of CS kidneys, whereas DecylTPP did not have any effect.

Example 5

CS Induced Renal Injury and Cell Death is Decreased with MitoQ Treatment

Figure 12A:
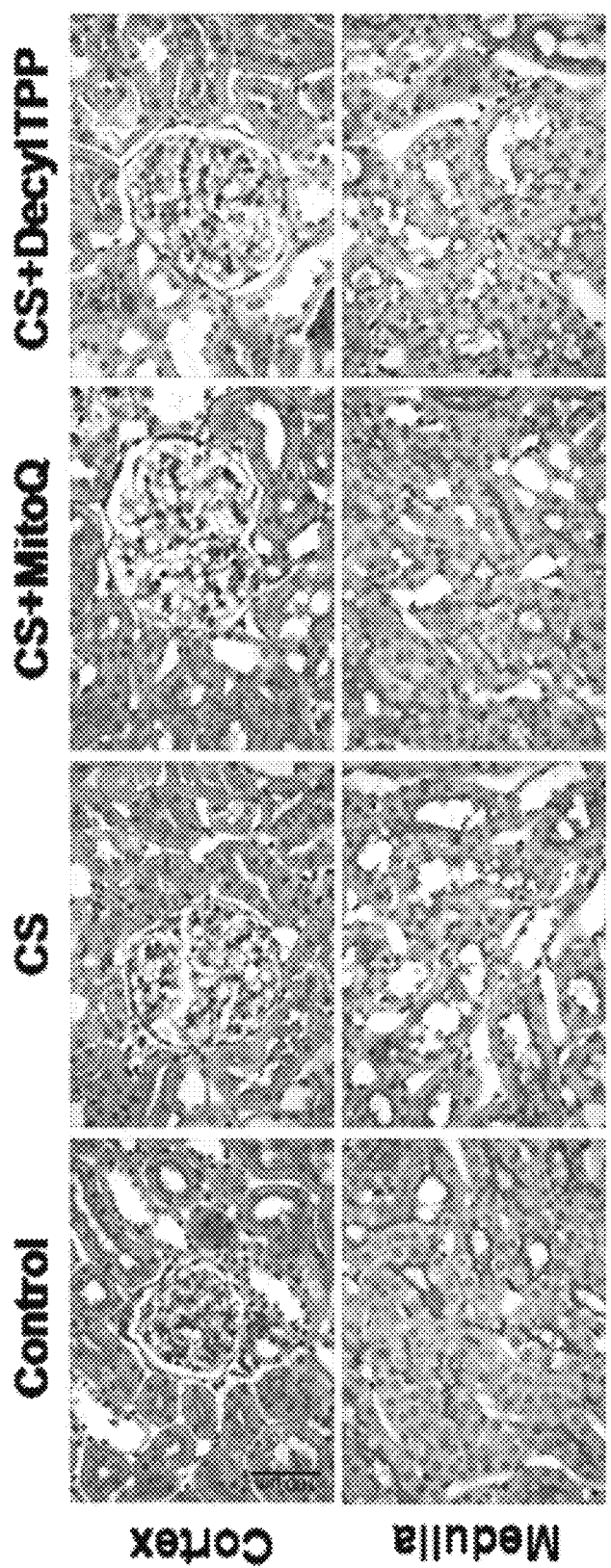
FIG. 12 depicts photomicrographs and plots showing the effect of MitoQ on CS-induced renal injury and cell death. Representative photomicrographs from five animal experiments are shown. (A) periodic acid-Schiff staining of rat kidneys (left to right): control, CS, CS+MitoQ (100 μM), and CS+DecylTPP (100 μM) (20×). Extensive tubular dilation, brush border loss, and cellular debris/tubular cast formation were observed and assessed blindly and semiquantitatively according to the following scoring system: 0, no changes; 1, mild changes; 2, moderate changes; and 3, severe changes. (B, C and D) Quantitation of tubular dilation. (E) TUNEL staining (brown nuclei; red arrows) of rat kidneys (left to right): control, CS, CS+MitoQ (100 μM), and CS+DecylTPP (100 μM) (40×). (F) The amount of cell death was calculated by averaging the number of cells positive for TUNEL in 10 different fields of the cortex and medulla. Values are expressed as mean±S.E.M. (n=5). ***, P<0.001 compared with control. †, P<0.05 compared with CS.
Figure 12:
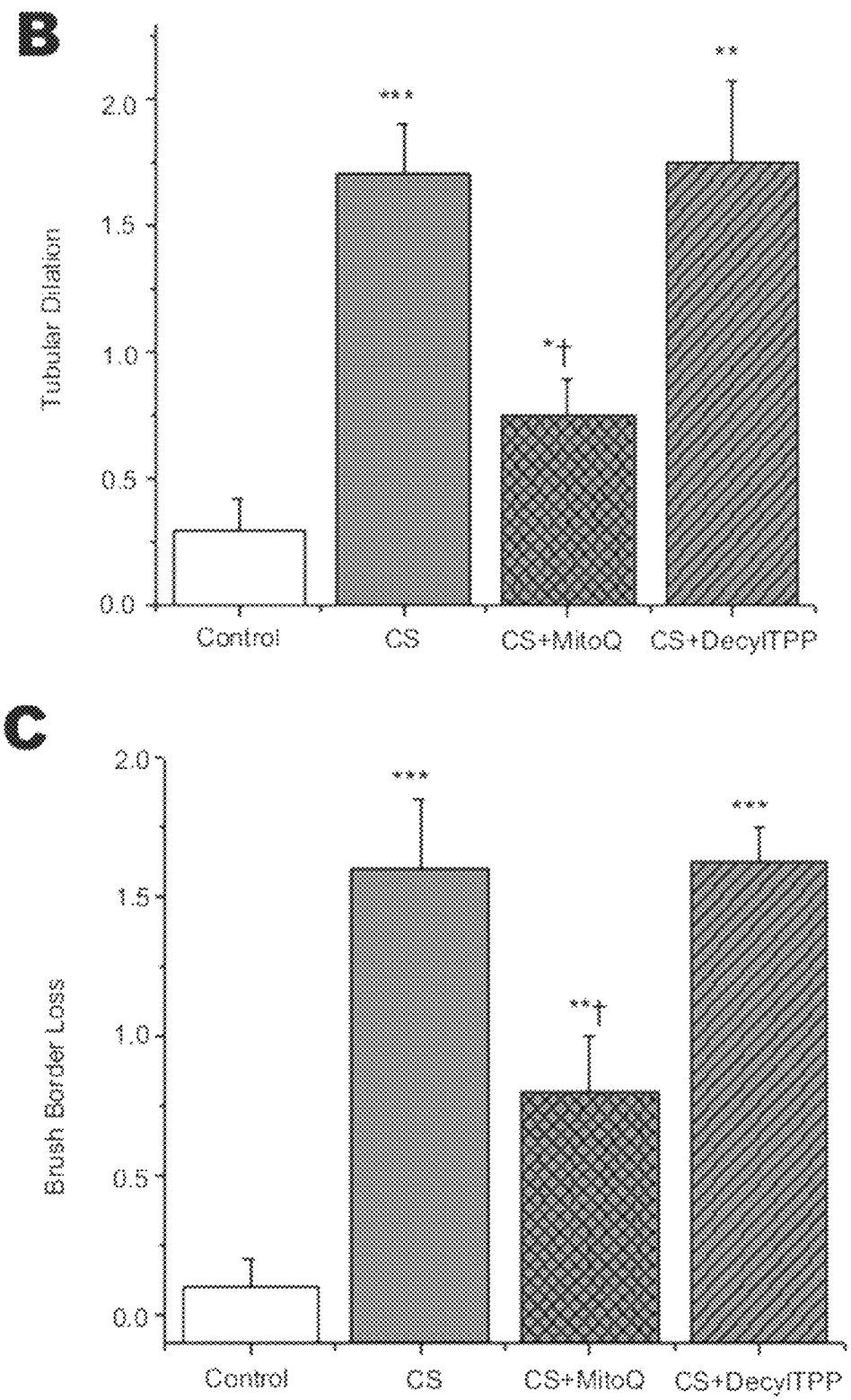
Figure 12D:
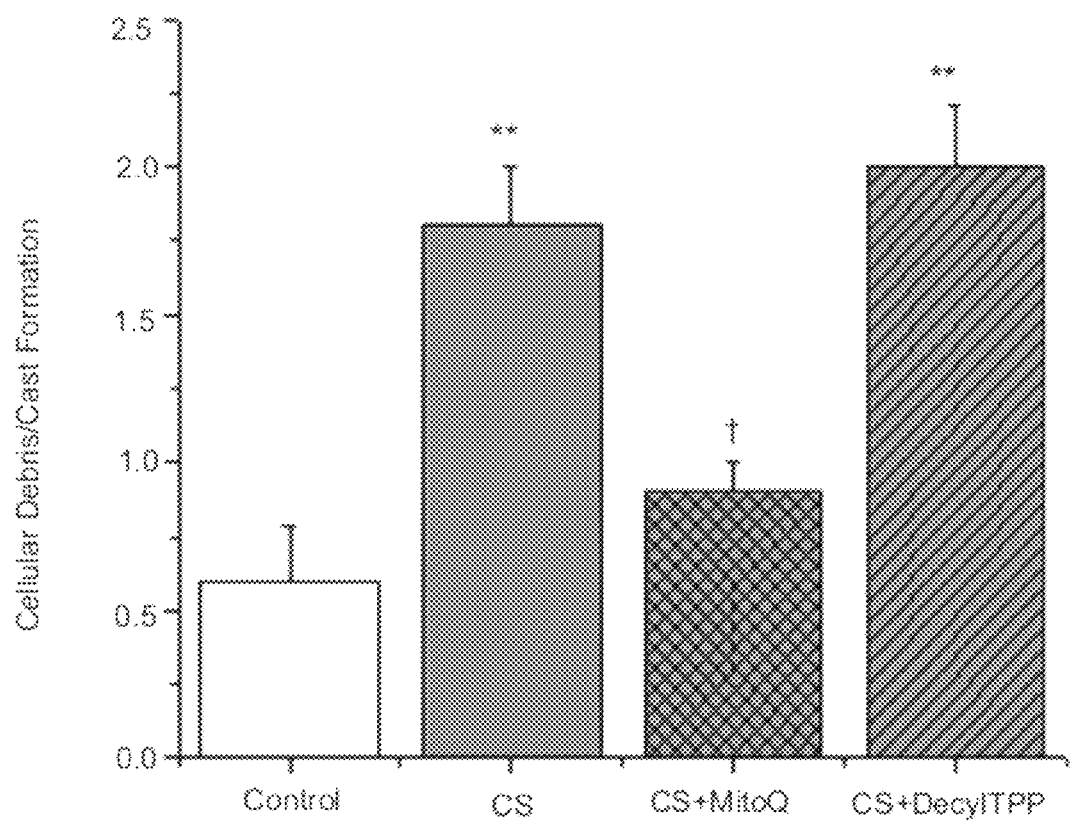
Figure 12E:
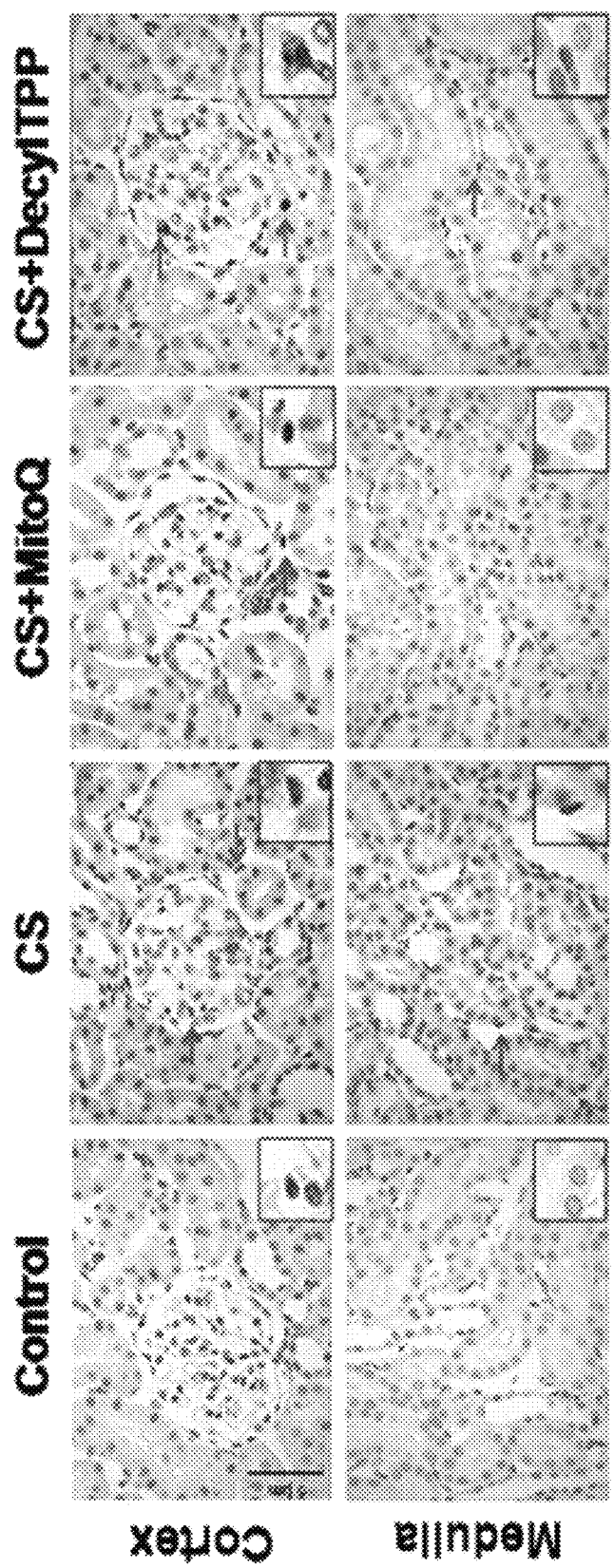
Figure 12F:
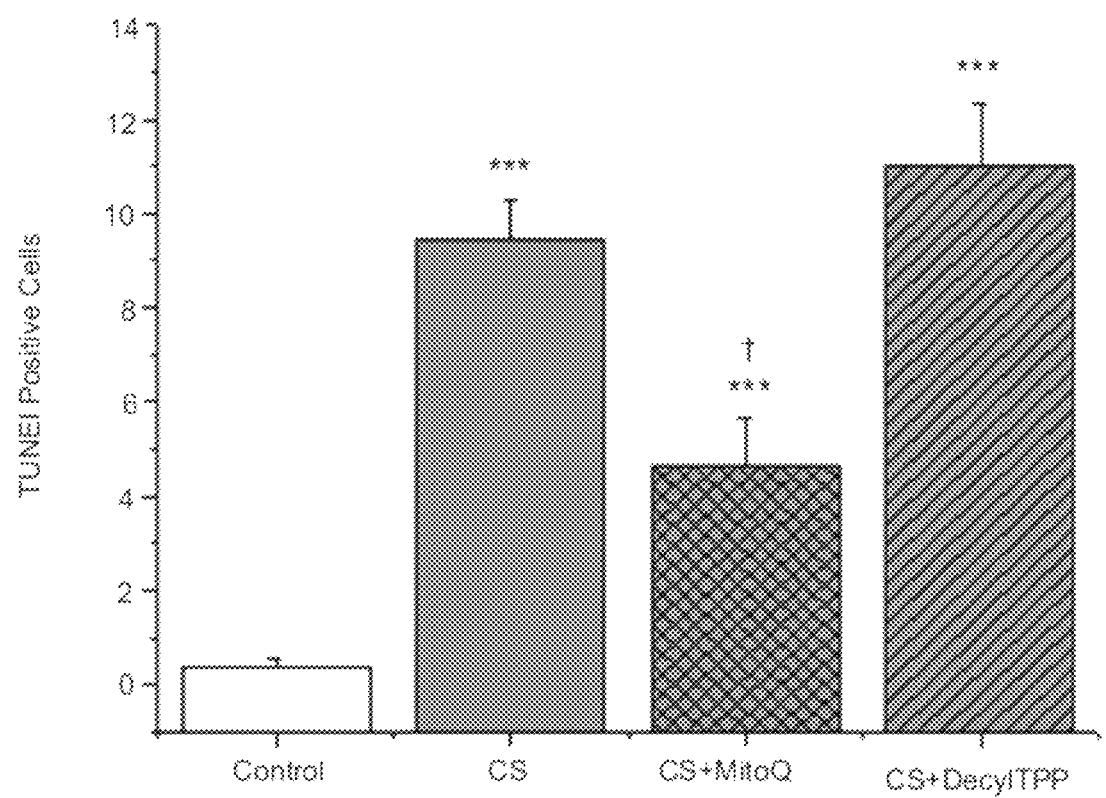

Periodic acid-Schiff staining was performed to examine histopathological changes during CS of rat kidneys. Significant widespread tubular damage such as dilation, brush border loss, and cellular debris/cast formation occurred with CS exposure (FIGS. 12A, B, C and D). MitoQ improved renal histology significantly, whereas DecylTPP treatment did not reverse renal injury. TUNEL staining, indicated by brown staining of the nuclei, was used as a marker of cell death. As shown in FIGS. 12E and F, CS led to a significant increase in cell death (red arrows) compared with control kidneys. MitoQ treatment decreased cell death by ~2-fold compared with CS kidneys, whereas DecylTPP offered no protective benefits against cell death.

Example 6

Figure 13A:
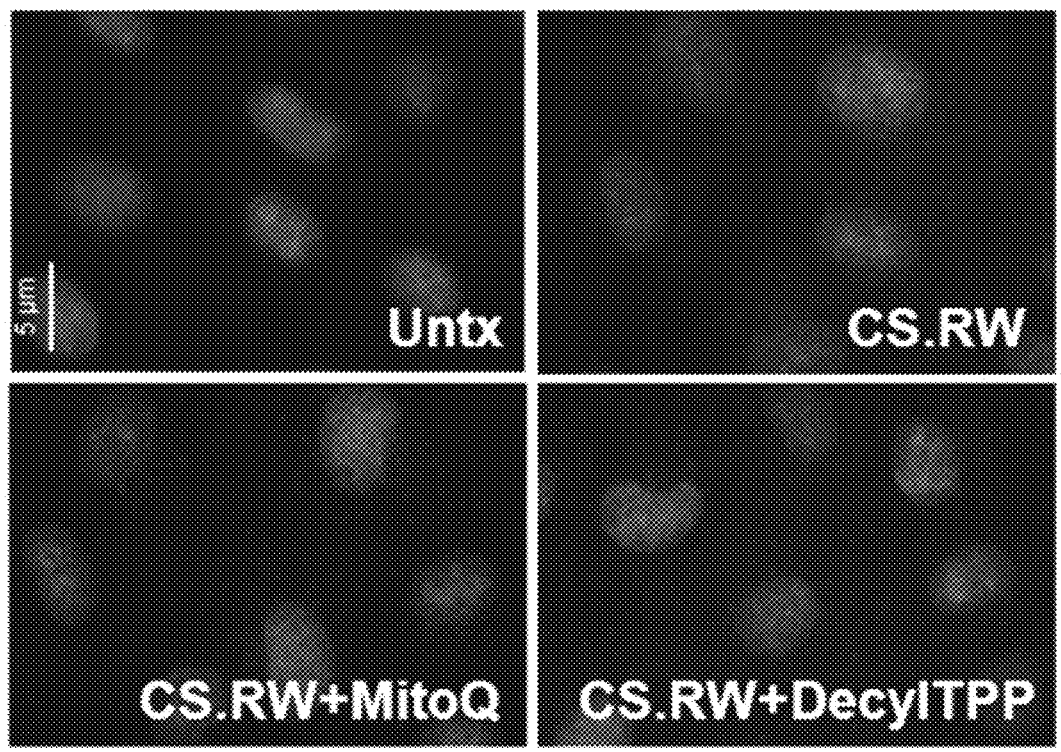
FIG. 13 depicts micrographs and plots showing that MitoQ decreases CS plus RW oxidant production and cell death. (A) fluorescence microscopic images of nitrotyrosine immunocytochemistry: untreated (Untx) cells and cells exposed to CS.RW (top) and cells exposed to CS.RW+MitoQ (1 μM) and CS.RW+DecylTPP (1 μM) (bottom) (40× oil). Results are representative of three experiments using different cell cultures. (B) Nitrotyrosine staining was quantified using the N is Elements software. Values are expressed as mean±S.E.M. (n=3). *, P<0.05 or *, P<0.001 compared with Untx cells; †, P<0.05 compared with CS.RW cells. (C) percentage of cell death was determined using the LDH Cytotoxicity Assay Kit II. Values are expressed as percentage of cell death means±S.E.M. (n=3). , P<0.01 or ***, P<0.001 compared with untreated cells. †, P<0.05 compared with CS cells. ‡, P<0.01 compared with CS.RW cells.
Figure 13B:
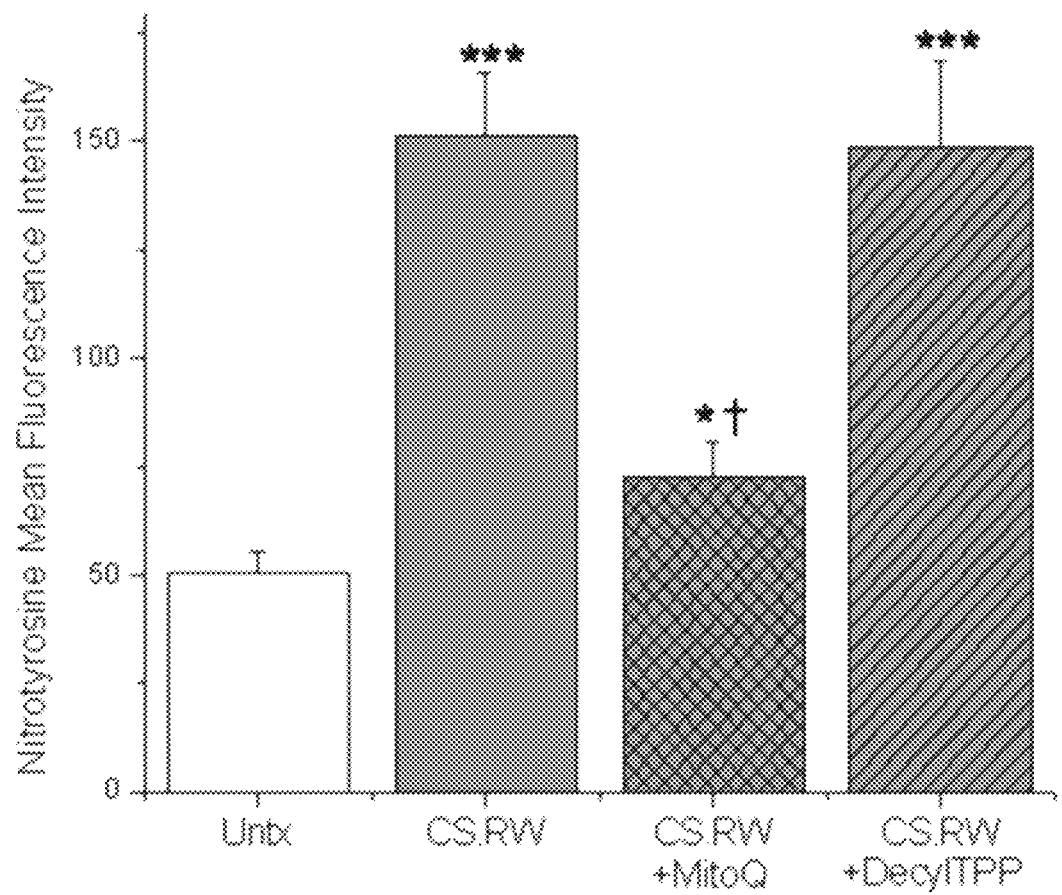
Figure 13C:
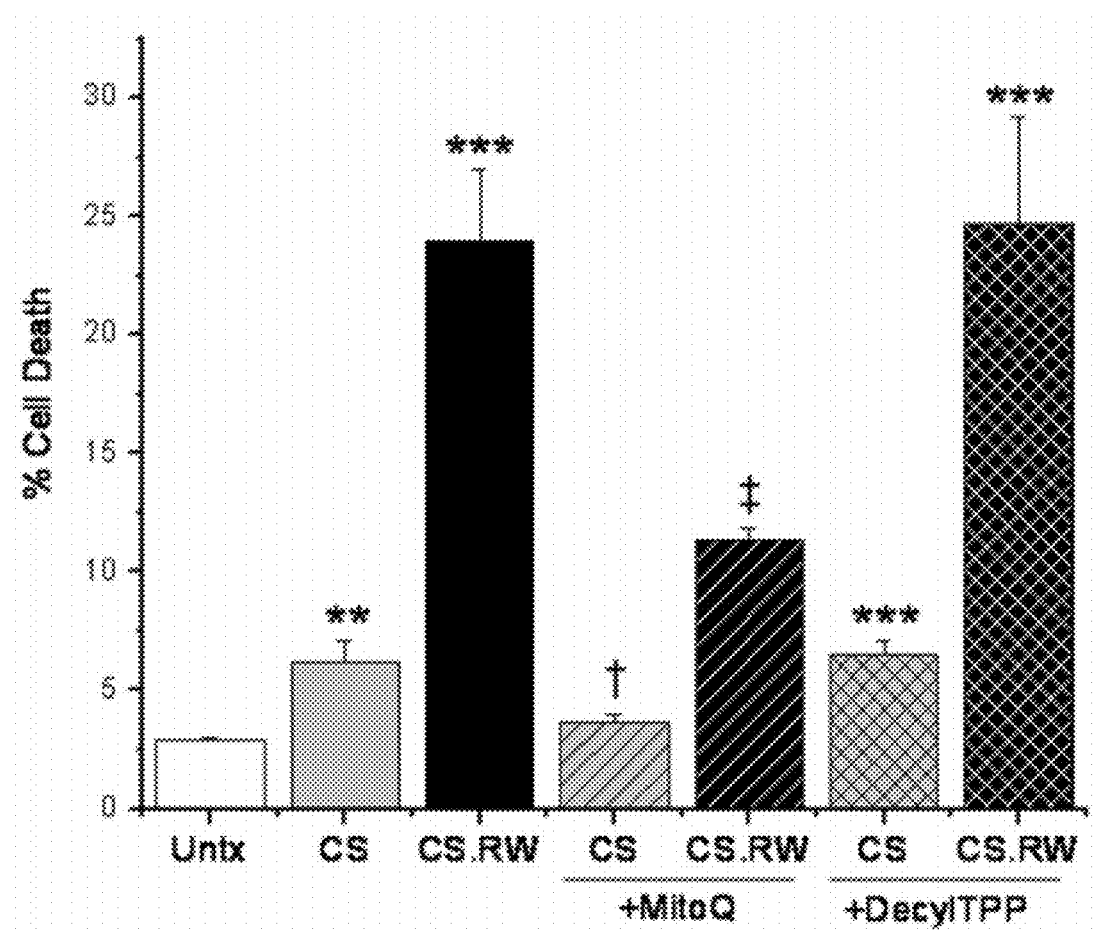

MitoQ Decreases Nitrotyrosine Formation and Cell Death During CS Plus Rewarming of NRK Cells To test whether MitoQ could potentially offer protection against oxidant production and cell death after reperfusion/transplantation, cells were exposed to CS plus RW. As shown in FIGS. 13A and B, 4-h CS plus overnight (18 h) RW of NRK cells resulted in significant nitrotyrosine formation. Adding MitoQ during CS attenuated nitrotyrosine staining significantly during CS.RW, whereas the control compound DecylTPP had no effect. LDH cytotoxicity revealed a significant increase in cell death of NRK cells exposed to CS.RW compared with untreated cells (FIG. 13C). MitoQ decreased cell death approximately 2-fold during CS alone and CS.RW. DecylTPP did not reduce cell death in either treatment group.

Discussion for Examples 2-6

In the present study, it was demonstrated that adding the mitochondria-targeted antioxidant MitoQ to UW preservation solution decreases oxidant production, prevents mitochondrial dysfunction, and minimizes renal injury and cell death during CS of NRK cells and isolated rat kidneys. MitoQ's control compound, DecylTPP (the lipophilic cation that targets MitoQ to the mitochondria), offered no protective effect and was included in this study as a negative control and to confirm MitoQ's antioxidative properties. It is important to point out that MitoQ was administered only during CS (4° C.) throughout this study. Thus, it is an ideal drug candidate for improving organ preservation because it would not require administration to the deceased donor before explantation or during organ reperfusion of the transplant recipient. During cold preservation of human organs, biopsies that evaluate renal damage are often used to determine whether to transplant or discard a donated kidney. Therefore, MitoQ's ability to reduce histological evidence of renal injury suggests that MitoQ might lead to fewer kidneys being discarded because of CS-mediated damage. Moreover, MitoQ has been proven to be safe and well tolerated in two phase II clinical trials for Parkinson's disease and hepatitis C virus, which could expedite its testing in clinical trials for use during organ preservation. In addition, MitoQ would not be administered systemically to patients, so potential drug-induced side effects would be greatly minimized. Results from the present study using markers of oxidative stress, mitochondrial function, and cellular injury provide substantial evidence of the effectiveness of MitoQ against CS-mediated injury and support the notion that mitochondrial ROS should be an important target in preventing cold preservation injury of donated kidneys.

Previous studies using human and porcine renal tubular cells have shown ROS, including superoxide (NADPH oxidase as the source), hydrogen peroxide, and hydroxyl radical to be major contributors to CS injury. A previous study has shown that mitochondrial ROS (superoxide, nitric oxide, and peroxynitrite) are signaling molecules that contribute to mitochondrial dysfunction and cell death of rat renal tubular cells exposed to CS (24 h) plus RW (6 h). It is important to point out that this previous study measured CS injury at a later time point (24 h) because most donated kidneys are preserved for extended periods. In the examples above, CS events were measured at 4 h to determine how early renal and mitochondrial injury occurs and to establish whether preventing early CS-mediated injury could avert downstream toxic events.

MitoQ's potential protective effects during CS were initially tested by measuring mitochondrial superoxide generation using MitoSOX Red. CS-induced mitochondrial superoxide was significantly reduced with MitoQ treatment, suggesting MitoQ would be highly effective in reducing downstream oxidant production and injury. Previous reports have shown MitoQ to decrease mitochondrial ROS specifically derived from superoxide in a hyperglycemic endothelial cell model and fenretinide-treated neuroblastoma cell lines. In addition, fenretinide treatment induced apoptosis of neuroblastoma tumors by increasing mitochondrial ROS production. Superoxide is the proximal oxidant that leads to the formation of other deleterious oxidants and can cause additional damage within the cell by entering the intermembrane space through the mitochondrial transition pore and/or through the voltage-dependent anion channel.

Nitric oxide is a free radical that is well known to interact with superoxide to form peroxynitrite. It is generated by nitric-oxide synthase (NOS) and is an important signaling molecule in many physiological processes. Few reports have evaluated the effect of cold ischemia alone on NOS protein levels or activity. Desrois et al. (2005, Transplant Proc. 37:4553) reported endothelial NOS protein levels to decrease significantly during cold ischemia and NOS activity to initially increase after 3-h ischemia but significantly declined after 6-h cold ischemia in a heterotopic rat heart transplantation model. Those authors suggested that cold ischemia induced endothelial dysfunction in the rat heart by decreasing nitric oxide's ability to exert its protective effects. Available nitric-oxide levels decline significantly after 24 h CS of NRK cells, the decrease probably caused by nitric oxide interacting with mitochondrial superoxide to form peroxynitrite. The fact that the NOS inhibitor $N^5$-[imino(methylamino)methyl]-L-ornithine citrate inhibited nitrotyrosine staining (one marker of peroxynitrite) strongly suggests that nitric oxide was indeed formed, but was quickly converted to peroxynitrite by interacting with superoxide. Additional studies using the CS NRK cell model showed that available nitric-oxide levels were also decreased after 4-h CS, and MitoQ had no effect (data not shown).

MitoQ's effectiveness against CS-induced mitochondrial superoxide warranted further evaluation of tyrosine nitration during CS of NRK cells and isolated rat kidneys. Formation of nitrotyrosine can adversely affect protein function and additional cellular processes. It was determined previously that cold UR of rat kidneys resulted in nitrotyrosine formation, and based on findings described in the Examples above, it is suggested that cold storage alone increases tyrosine nitration. MitoQ was able to markedly reduce nitrotyrosine in both the cellular and isolated kidney models. After detoxifying oxidants, MitoQ can be reduced by the respiratory chain to be repeatedly recycled back to its antioxidant form, which further supports the advantage of adding MitoQ during CS because it is able to continuously scavenge oxidants. Taken together, the results shown in the Examples suggest that adding MitoQ to UW solution attenuates oxidative stress during CS by scavenging mitochondrial superoxide.

Increased oxidant production can lead to mitochondrial respiratory complex inactivation, decline in adenosine triphosphate levels, mitochondrial dysfunction, and consequently cell death. Cold preservation has been shown to impair mitochondrial function in many organ systems. Data presented in the Examples above reveal that CS leads to partial inactivation of mitochondrial complexes I and II in both the cellular and ex vivo kidney models and excitingly was completely prevented with MitoQ treatment. Protecting complex I and II activity is important because these complexes initiate oxidative phosphorylation and can generate additional oxidants once inactivated. MitoQ has been shown to restore mitochondrial function in a rodent model of cardiac dysfunction induced by sepsis. Also, cardiac mitochondrial dysfunction in this model was associated with a significant increase in ROS generation. Thus, MitoQ's ability to restore CS respiratory complex activity could explain the reduction in mitochondrial superoxide generation also observed with MitoQ.

Both cold ischemia-mediated oxidant production and mitochondrial dysfunction can lead to irreversible renal injury and cell death that can result in further damage once the organ is transplanted. It has been shown that loss of tubular brush border is a clear indicator of ischemic injury and a sign of impaired proximal tubular function, which can ultimately lead to cell death. In the Examples above, MitoQ protected against CS-mediated renal injury by decreasing tubular brush border loss, tubular dilation, and cell death.

The extent of protection observed with MitoQ during CS alone clearly indicates that renal function would most likely be improved, and as mentioned earlier protection during CS alone could translate into fewer kidneys being discarded. Collectively, these findings suggest that the mechanisms leading to cell death during CS.RW seem to be initiated during CS alone and can be modulated with antioxidant treatment.

In summary, this is the first report showing that mitochondrial superoxide increases significantly during early CS and contributes to mitochondrial and renal damage. We have identified the mitochondria-targeted antioxidant MitoQ to significantly protect against CS-mediated oxidative stress, mitochondrial dysfunction, cell death, and renal injury of renal proximal tubular cells and isolated rat kidneys. These findings suggest that infusion of MitoQ to kidneys before transplantation may be of therapeutic use to reduce CS damage, improve outcome for transplant recipients, and also increase the numbers of donated organs available for transplant, all of which could lead to a decline in health-care costs.

Example 7

MitoQ Protects Porcine Kidneys

Figure 14A:
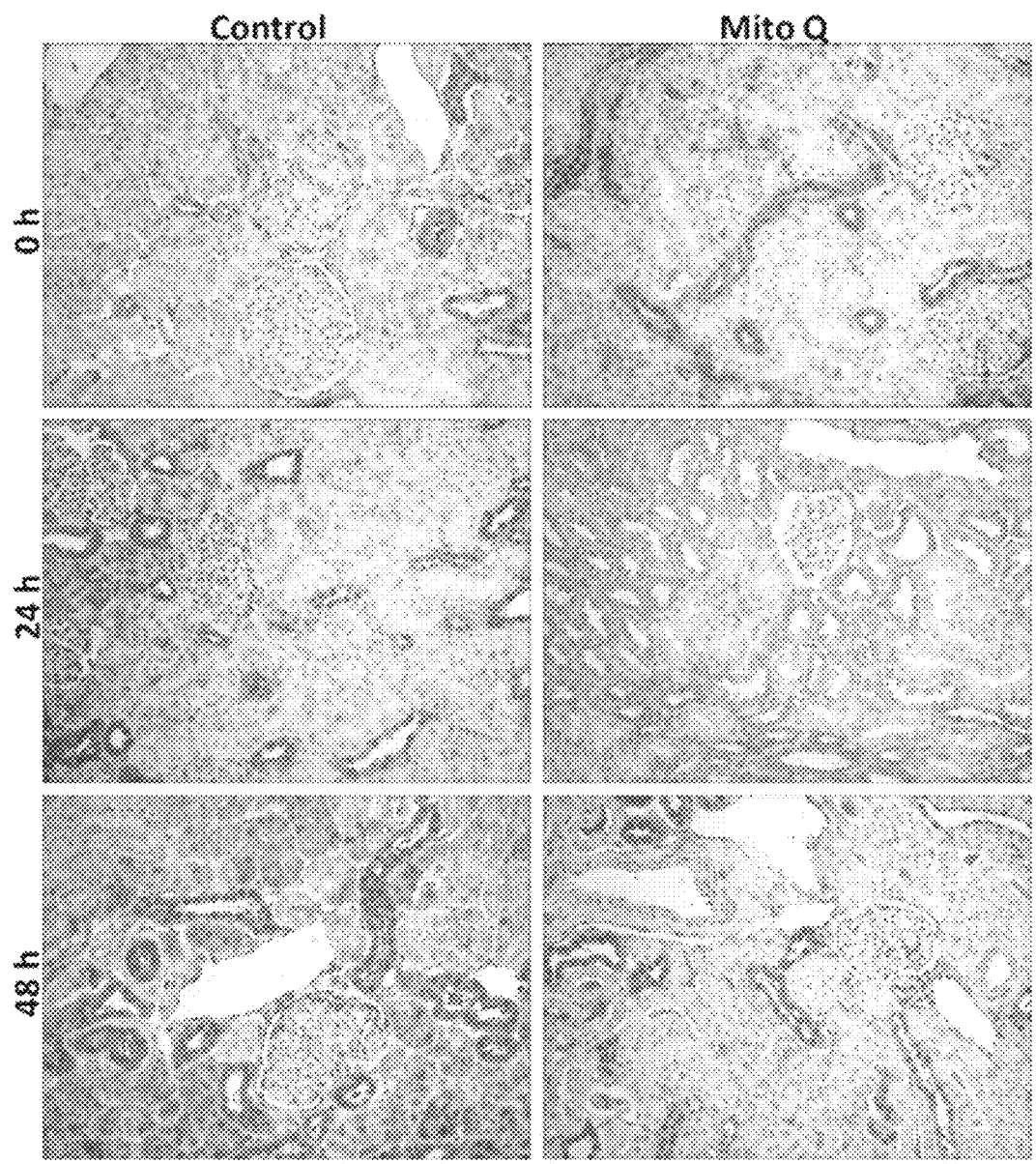
FIG. 14 depicts micrographs and plots showing increased nitrotyrosine protein expression detected during cold preservation. (A) Representative images showing MitoQ (100 mM) mediated reduction of nitrotyrosine staining. (B) Expression level of total (combined cortex and medulla) nitrotyrosine was evaluated and scored. (C) Expression level of cortical and medulla nitrotyrosine was evaluated and scored. Error bar indicates Mean SEM (n=4). *P<0.05 compared to untreated kidneys at 24 and 48 hr within the cortex.
Figure 14:
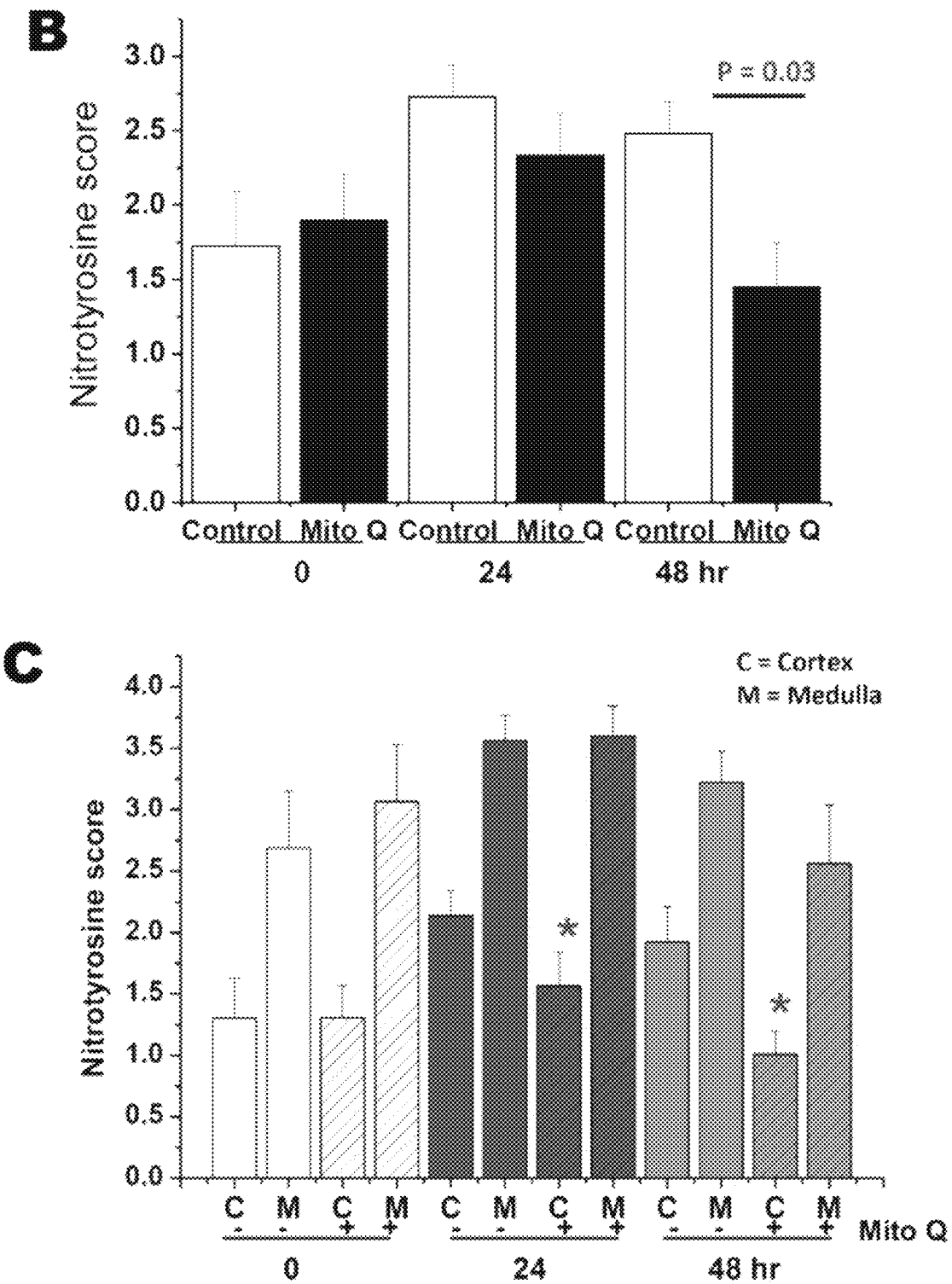

Nitrotyrosine staining and nitrotyrosine expression levels were used to determine protective effect of MitoQ on porcine kidneys during SC. Treatment with MitoQ significantly decreased nitrotyrosine staining during SC (FIG. 14A). Quantitation of nitrotyrosine staining also showed that nitrotyrosine expression levels, when measured in combined cortex and medulla were also reduced (FIG. 14B). Significantly, nitrotyrosine expression levels were significantly lower in the cortex (FIG. 14C).

Figure 15:
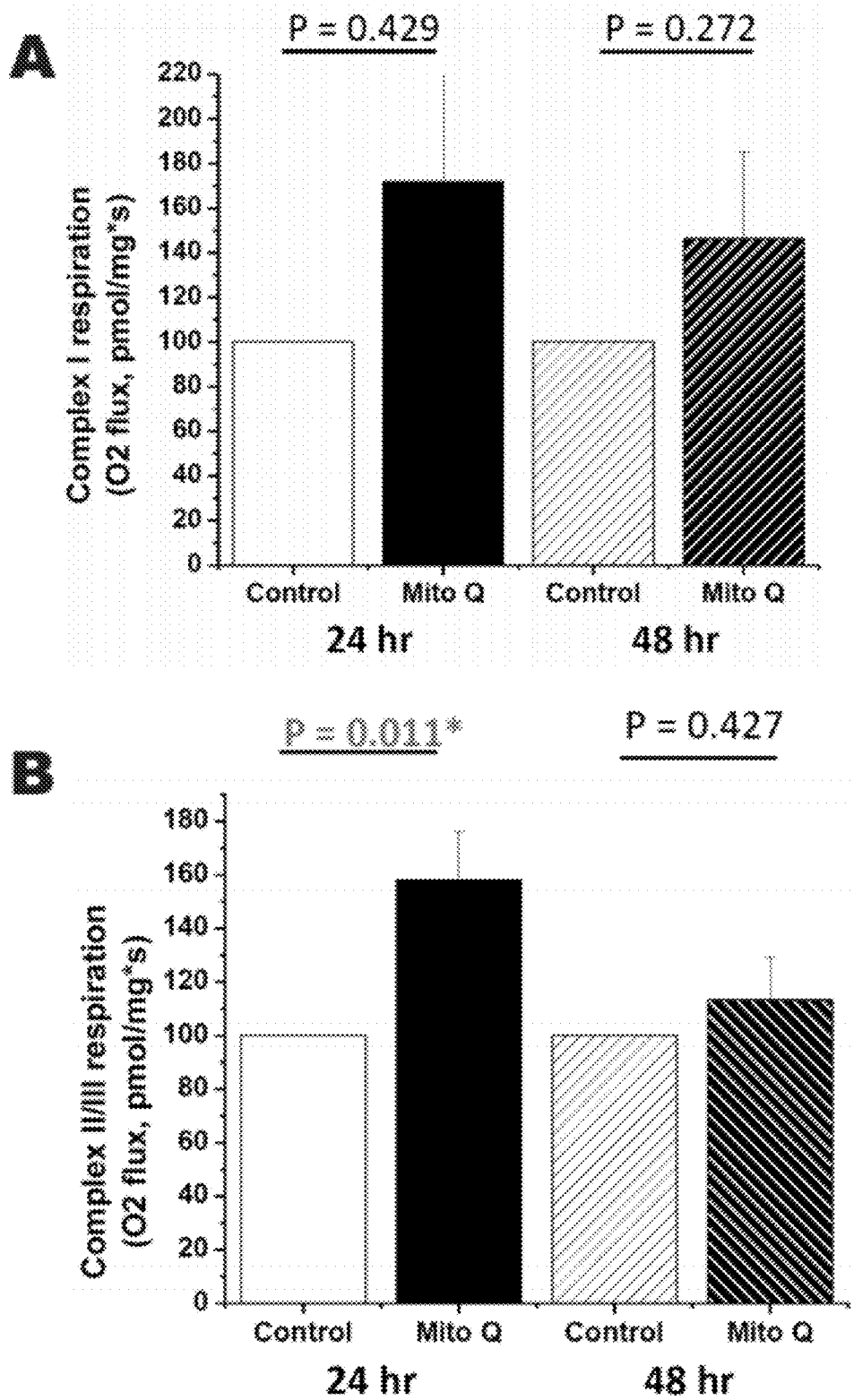
FIG. 15 depicts graphs showing activities or (A) porcine renal mitochondrial respiratory complex I, (B) activities or porcine renal mitochondrial respiratory complex II/III, and (C) activities or porcine renal mitochondrial respiratory complex IV, after MitoQ treatment. MitoQ (100 mM) protected porcine complex II/III following 24 hr cold preservation. Values are expressed as mean SEM (n=4).
Figure 15C:
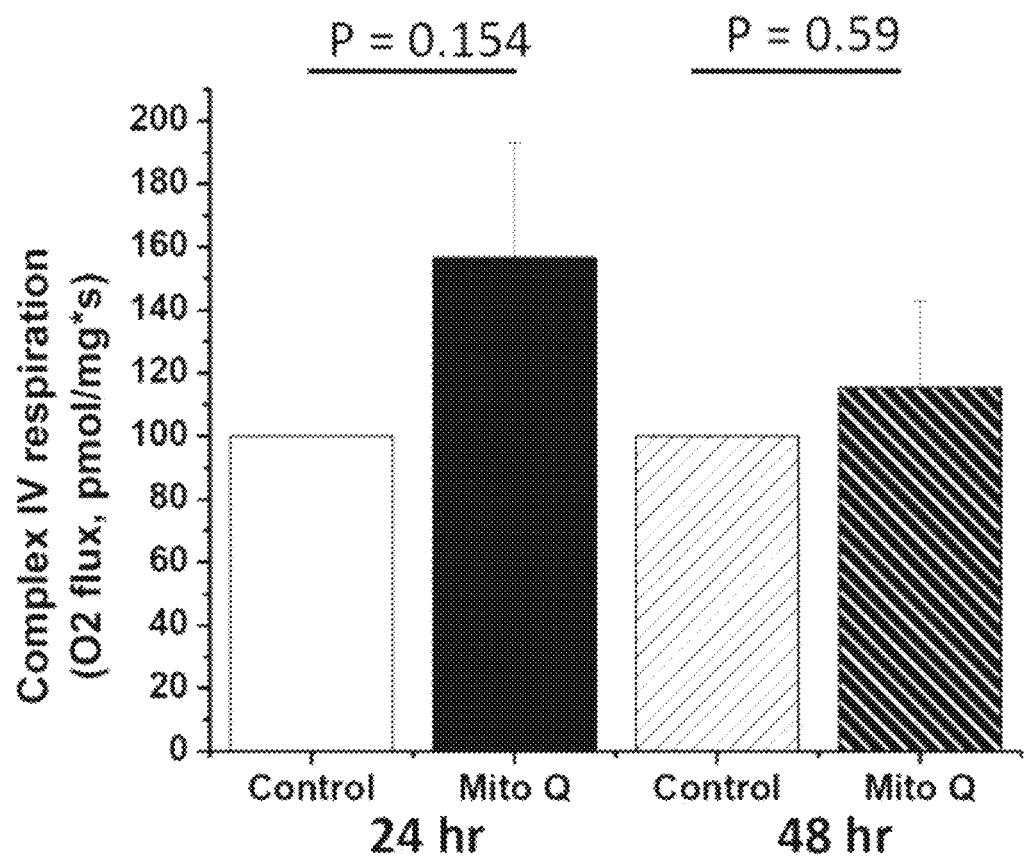

Mitochondrial respiratory complex activity was also evaluated in the porcine ex vivo renal model at 24-h and 48-h CS. MitoQ prevented Complexes I II/III and IV at 24-h better than at 48-h (FIG. 15). Protection of Complex II/III by MitoQ (100 µM) was significant following 24-h cold preservation.

What is claimed is:

1. A method of reducing oxidative damage to an organ that occurs during cold storage, the method comprising (i) contacting the organ with a composition comprising mitoquinone and an organ preservation solution, wherein the organ first contacts the composition during cold storage of the organ, and wherein the subject is selected from the group consisting of a rodent, a human, a zoological animal, a companion animal, and a livestock animal; and (ii) cold storing the organ in the composition for at least thirty minutes, such that the composition reduces oxidative damage to an organ that occurs during cold storage.

2. The method of claim 1, wherein the method further comprises measuring oxidative damage to the organ and the oxidative damage is measured by complex I activity, complex II activity, complex III activity, complex IV activity, or a combination thereof.

3. The method of claim 1, wherein the method further comprises measuring oxidative damage to the organ and the oxidative damage is measured by MnSOD activity.

4. The method of claim 1, wherein the method further comprises measuring oxidative damage to the organ and the oxidative damage is measured by measuring creatinine clearance.

5. The method of claim 1, wherein the method further comprises measuring oxidative damage to the organ and the oxidative damage is measured by measuring nitrotyrosine adduct formation.

6. The method of claim 1, wherein the method further comprises measuring oxidative damage to the organ and the oxidative damage is measured by measuring superoxide generation.

7. The method of claim 1, wherein the organ is a kidney.

8. A method of reducing oxidative damage to a kidney that occurs during cold storage, the method comprising (i) contacting the kidney with a composition comprising mitoquinone and an organ preservation solution, wherein the kidney first contacts the composition during cold storage of the kidney, and wherein the subject is selected from the group consisting of a rodent, a human, a zoological animal, a companion animal, and a livestock animal; and (ii) cold storing the kidney in the composition for at least thirty minutes, such that the composition reduces oxidative damage to a kidney that occurs during cold storage.

9. The method of claim 8, wherein the method further comprises measuring oxidative damage to the organ and the oxidative damage is measured by complex I activity, complex II activity, complex III activity, complex IV activity, or a combination thereof.

10. The method of claim 8, wherein the method further comprises measuring oxidative damage to the organ and the oxidative damage is measured by MnSOD activity.

11. The method of claim 8, wherein the method further comprises measuring oxidative damage to the organ and the oxidative damage is measured by measuring creatinine clearance.

12. The method of claim 8, wherein the method further comprises measuring oxidative damage to the organ and the oxidative damage is measured by measuring nitrotyrosine adduct formation.

13. The method of claim 8, wherein the method further comprises measuring oxidative damage to the organ and the oxidative damage is measured by measuring superoxide generation.

14. A method of reducing oxidative damage to an organ that occurs during cold storage prior to transplantation of the organ, the method comprising (i) contacting the organ with a composition comprising mitoquinone and an organ preservation solution, wherein the organ first contacts the composition during cold storage of the organ, and wherein the subject is selected from the group consisting of a rodent, a human, a zoological animal, a companion animal, and a livestock animal; and (ii) cold storing the organ in the composition, such that the composition reduces oxidative damage to an organ that occurs during cold storage before transplantation and preserves organ quality for transplantation.

15. The method of claim 14, wherein the method further comprises measuring oxidative damage to the organ and the oxidative damage is measured by complex I activity, complex II activity, complex III activity, complex IV activity, or a combination thereof.

16. The method of claim 14, wherein the method further comprises measuring oxidative damage to the organ and the oxidative damage is measured by MnSOD activity, superoxide generation, or nitrotyrosine adduct formation.

17. The method of claim 1, wherein the method further comprises measuring oxidative damage to the organ and the oxidative damage is measured by measuring creatinine clearance.

* * * * *